US008674144B2

(12) United States Patent
Yamada et al.

(10) Patent No.: US 8,674,144 B2
(45) Date of Patent: Mar. 18, 2014

(54) CATALYST FOR ASYMMETRIC HYDROGENATION AND METHOD FOR MANUFACTURING OPTICALLY ACTIVE CARBONYL COMPOUND USING THE SAME

(75) Inventors: Shinya Yamada, Kanagawa (JP); Hironori Maeda, Kanagawa (JP); Yoji Hori, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 32 days.

(21) Appl. No.: 13/304,925

(22) Filed: Nov. 28, 2011

(65) Prior Publication Data
US 2012/0136176 A1 May 31, 2012

(30) Foreign Application Priority Data

Nov. 29, 2010 (JP) .................................. 2010-265555

(51) Int. Cl.
*C07C 45/62* (2006.01)
*B01J 31/28* (2006.01)
(52) U.S. Cl.
USPC .......................................... 568/459; 502/167
(58) Field of Classification Search
USPC .......................................... 568/459; 502/167
See application file for complete search history.

(56) References Cited

U.S. PATENT DOCUMENTS

| 4,237,072 | A | 12/1980 | Aviron-Violet et al. |
| 2006/0161024 | A1 | 7/2006 | MacMillan et al. |
| 2008/0269528 | A1 | 10/2008 | Jakel et al. |

FOREIGN PATENT DOCUMENTS

| JP | 54-14911 | 2/1979 |
| JP | 2008-515843 A | 5/2008 |
| WO | 2010061909 A1 | 6/2010 |

OTHER PUBLICATIONS

Akagawa et al., "Asymmetric transfer hydrogenation in aqueous media catalyzed by resin-supported peptide having a polyleucine tether", Tetrahedron: Asymmetry, 2009, vol. 20, pp. 461-466.
Davie, et al., "Asymmetric Catalysis Mediated by Synthetic Peptides", Chemical Review, 2007, vol. 107, No. 12, pp. 5759-5812.
Farkas, et al., "Enantioselective hydrogenation of isophorone over Pd catalyts in the presence of (-)-dihydroapovincaminic acid ethyl ester", Journal of Molecular Catalysis A: 2001, vol. 170, pp. 101-107.
Farkas, et al., "New chiral auxiliaries in enantioselective heterogeneous catalytic hydrogenations", Journal of Molecular Catalysis A: Chemical 1999 vol. 138, pp. 123-127.
Fogassy, et al., "Enantioselective hydrogenation of exocyclic a,β-unsaturated ketones", Journal of Molecular Catalysis A: Chemical 2002, vol. 179, pp. 101-106.
Fogassy, et al., "Enantioselective hydrogenation of exocyclic a,β-unsaturated ketones", Journal of Molecular Catalysis A: Chemical, 2003, vol. 192, pp. 189-194.
Oueliet, et al., "Enantioselective Organocatalytic Transfer Hydrogenation Reactions using Hantzsch Esters", Accounts of Chemical Research, 2007, vol. 40, pp. 1327-1339.
Sipos, et al., "Enantioselective hydrogenation of isophorone with titania supported Pd catalysts modified by (-)-dihydroapovincaminic acid ethyl ester effect of the support and the reduction method", Journal of Molecular Catalysis A: Chemical 2002, vol. 179, pp. 107-112.
European Search Report dated Nov. 13, 2012 issued by the European Patent Office in corresponding European Patent Application No. 11190416.5.
Tungler, et al., "Enantioselective Hydrogenation of α-β-Unsaturated Ketones", Catalysis Today, Elsevier Science Publishers B.V., 1989, pp. 159-171, XP55040684.
"Liquid-phase synthesis of phagocytosis-stimulating tetrapeptide tuftsin", Chemical Abstracts Service, XP002685874, 2009 (1 page), and CN101550180A, Oct. 7, 2009, 10 pages.
"Hydrogenolysis of N-carbobenzoxyprolylarginine on a commercial palladium/carbon catalyst", Chemical Abstracts Service, 1984, XP2685875.
Prabhakaran, et al., "π-facial selectivity in polyniline supported cobalt catalysed aerobic epoxidation of N-cinnamoyl proline deratives", Tetrahedron Letters, Jan. 8, 2001, pp. 333-337, XP004227768.
Ueno, et al., "Size-Selective Olefin Hydrogenation by a Pd nanocluster Provided in an Apo-Ferritin Cage", Angewandte Chemie, vol. 43, No. 19, May 3, 2004, pp. 2527-2530, XP002549575;, and Granier, et al., "Comparison of the Structure of the Cubic and Tetragonal Forms of Horse-Spleen Apoferritin", Acta Crystallographica Section D: Biological Crystallography, vol. 53, No. 5, Sep. 1, 1997, pp. 580-587, XP55040744.

*Primary Examiner* — Sikarl Witherspoon
(74) *Attorney, Agent, or Firm* — Sughrue Mion, PLLC

(57) ABSTRACT

The present invention provides a catalyst used for manufacturing an optically active carbonyl compound by selective asymmetric hydrogenation of an α,β-unsaturated carbonyl compound, which is insoluble in a reaction mixture, and a method for manufacturing the corresponding optically active carbonyl compound. Particularly, the invention provides a catalyst for obtaining an optically active citronellal useful as a flavor or fragrance, by selective asymmetric hydrogenation of citral, geranial or neral. The invention relates to a catalyst for asymmetric hydrogenation of an α,β-unsaturated carbonyl compound, which comprises: a powder of at least one metal selected from metals belonging to Group 8 to Group 10 of the Periodic Table, or a metal-supported substance in which the at least one metal is supported on a support; an optically active peptide compound; and an acid, and also relates to a method for manufacturing an optically active carbonyl compound using the same.

4 Claims, No Drawings

CATALYST FOR ASYMMETRIC HYDROGENATION AND METHOD FOR MANUFACTURING OPTICALLY ACTIVE CARBONYL COMPOUND USING THE SAME

CROSS-REFERENCE TO RELATED APPLICATIONS

This application claims priority from Japanese Patent Application No. 2010-265555 filed on Nov. 29, 2010, the entire subject matter of which is incorporated herein by reference.

BACKGROUND OF THE INVENTION

1. Technical Field of the Invention

The present invention relates to a method for manufacturing an optically active aldehyde or optically active ketone, which is an optically active carbonyl compound, by conducting selective asymmetric hydrogenation of carbon-carbon double bond of an $\alpha,\beta$-unsaturated carbonyl compound by using a catalyst for asymmetric hydrogenation.

2. Background Art

Conventionally, there have been made attempt for conducting asymmetric hydrogenation of carbon-carbon double bond of $\alpha,\beta$-unsaturated aldehyde using hydrogen gas, and there is known method for conducting asymmetric hydrogenation of neral or geranial for the purpose of obtaining optically active citronellal which is important particularly as a flavor or fragrance (Patent Literatures 1 and 2). Since these methods are methods for hydrogenating carbon-carbon double bond with hydrogen gas using a small amount of a homogeneous catalyst, auxiliaries are not required so that a large amount of waste is not generated.

There have been reported asymmetric hydrogenation of carbon-carbon double bond of $\alpha,\beta$-unsaturated ketone using a combination of Pd black, Pd/C or Pd/TiO$_2$ and (-)-dihydroapovincamic acid ethyl ester, proline or cinchonidine (Non-Patent Literatures 1 to 5)

There has been reported hydrogen transfer type asymmetric hydrogenation reaction of an $\alpha,\beta$-unsaturated compound using an organic asymmetric catalyst and Hantzsch ester (Patent Literature 3 and Non-patent Literature 6).

Further, there has been reported asymmetric catalyst reaction using only a peptide compound (Non-patent Literature 7). Furthermore, there has been reported hydrogen transfer type asymmetric hydrogenation reaction of an $\alpha,\beta$-unsaturated compound using a peptide compound and Hantzsch ester (Non-patent Literature 8).

Patent Literatures

Patent Literature 1: JP-A-54-14911
Patent Literature 2: JP-T-2008-515843 (the term "JP-T" as used herein means a published Japanese translation of a PCT patent application)
Patent Literature 3: US 2006/0161024

Non-Patent Literatures

Non-Patent Literature 1: Journal of Molecular Catalysis A: Chemical 1999, 138, 123-127
Non-Patent Literature 2: Journal of Molecular Catalysis A: Chemical 2001, 170, 101-107
Non-Patent Literature 3: Journal of Molecular Catalysis A: Chemical 2002, 179, 101-106
Non-Patent Literature 4: Journal of Molecular Catalysis A: Chemical 2002, 179, 107-112
Non-Patent Literature 5: Journal of Molecular Catalysis A: Chemical 2003, 192, 189-194
Non-Patent Literature 6: Acc. Chem. Res. 2007, 40, 1327-1339
Non-Patent Literature 7: Chem. Rev. 2007, 107, 5759-5812
Non-Patent Literature 8: Tetrahedron: Asymmetry, 2009, 20, 461-466.

SUMMARY OF THE INVENTION

However, the catalyst used by the methods of Patent Literatures 1 and 2 is a homogeneous catalyst which uses expensive rhodium metals and the like, and it is difficult to recover the catalyst because it dissolves in the reaction mixture.

In the methods of Non-Patent Literatures 1 to 5, there are examples using only isophorone and a special exocyclic ketone, and the catalyst system of the invention is not used.

The methods of using organic catalyst described in Non-Patent Literature 6, Non-Patent Literature 7, Non-Patent Literature 8 and Patent Literature 3 are economically disadvantageous as a method for producing an optically active aldehyde or an optically active ketone, because a catalyst quantity of about 20% by mol based on the raw material unsaturated aldehyde or unsaturated ketone is required and the Hantzsch ester as the substrate of hydrogenation is required in an amount of equal to or larger than the raw material unsaturated aldehyde or unsaturated ketone.

Accordingly, concern has been directed toward the development of a method for easily recovering a catalyst by the use of heterogeneous catalyst such as a solid catalyst which does not dissolve in the reaction mixture.

In addition, an asymmetric hydrogenation reaction of an $\alpha,\beta$-unsaturated aldehyde using heterogeneous catalyst such as a solid catalyst has not been known.

An object of the invention relates to a method for conducting asymmetric hydrogenation of carbon-carbon double bond of an $\alpha,\beta$-unsaturated carbonyl compound using, as a catalyst for asymmetric hydrogenation, a heterogeneous catalyst which can be easily separated from the reaction mixture and thereby obtaining corresponding optically active aldehyde or optically active ketone. Particularly, it relates to a method for obtaining optically active citronellal by hydrogenating citral, geranial or neral by asymmetric hydrogenation reaction.

The inventors have conducted intensive studies with the aim of solving the above-mentioned problems and found as a result that a corresponding optically active aldehyde or optically active ketone can be obtained by conducting asymmetric hydrogenation of an $\alpha,\beta$-unsaturated carbonyl compound using a specified metal powder or metal-supported substance, an optically active peptide compound and an acid, thereby resulting in the accomplishment of the invention.

In addition, after completion of the reaction, the optically active peptide compound and metal powder or metal-supported substance can be easily recovered from the reaction system and reused again as the catalyst for asymmetric hydrogenation.

That is, the present invention encompasses the following embodiments.

[1] A catalyst for asymmetric hydrogenation of an $\alpha,\beta$-unsaturated carbonyl compound, which comprises:
a powder of at least one metal selected from metals belonging to Group 8 to Group 10 of the Periodic Table, or a metal-supported substance in which at least one metal selected from metals belonging to Group 8 to Group 10 of the Periodic Table is supported on a support;

an optically active peptide compound represented by the following general formula (1):

[Chem. 1]

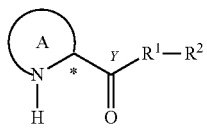

(1)

wherein ring A is a 3- to 7-membered ring which may have a substituent group, contains at least one atom selected from the group consisting of a carbon atom, a nitrogen atom, a sulfur atom, an oxygen atom and a phosphorus atom, and may be a fused ring structure; $R^1$ represents an amino acid residue which is bonded to a carbonyl group at Y-position by a peptide bond or a peptide residue which is constituted from 2 to 30 amino acids and is bonded to a carbonyl group at Y-position by a peptide bond; $R^2$ represents an amino group which is bonded to a carbonyl group at C-terminus of $R^1$, an alkoxy group which is bonded to a carbonyl group at C-terminus of $R^1$, a hydroxy group which is bonded to a carbonyl group at C-terminus of $R^1$ or a polymer chain which is bonded to a carbonyl group at C-terminus of $R^1$, and * represents an asymmetric carbon atom; and an acid.

[2] The catalyst for asymmetric hydrogenation according to [1], wherein the metal is selected from the group consisting of nickel, ruthenium, rhodium, iridium, palladium and platinum.

[3] A method for manufacturing an optically active carbonyl compound represented by the following general formula (3):

[Chem. 2]

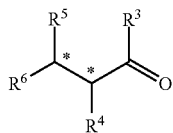

(3)

wherein $R^3$, $R^4$, $R^5$ and $R^6$ are the same as defined in the following formula (2), and two * mean that at least one * represents an asymmetric carbon atom, wherein the method comprises conducting asymmetric hydrogenation of an α,β-unsaturated carbonyl compound represented by the following general formula (2) by using the catalyst for asymmetric hydrogenation according to [1] or [2]:

[Chem. 3]

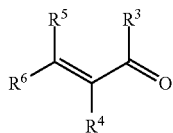

(2)

wherein $R^3$, $R^4$, $R^5$ and $R^6$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, an alkoxycarbonyl group which may have a substituent group or an aralkyloxy group which may have a substituent group; $R^3$ and $R^4$, $R^3$ and $R^5$, $R^3$ and $R^6$, $R^4$ and $R^6$ or $R^5$ and $R^6$ may form a ring; and when a ring is not formed by $R^3$ and $R^4$ or $R^3$ and $R^5$, and $R^4$ does not represent a hydrogen atom, $R^5$ and $R^6$ may be the same or different from each other; and when a ring is not formed by $R^3$ and $R^4$ or $R^3$ and $R^5$, and $R^4$ represents a hydrogen atom, $R^5$ and $R^6$ do not represent a hydrogen atom and are different from each other.

[4] The method according to [3], wherein the α,β-unsaturated carbonyl compound is geranial, neral or citral.

[5] The method according to [3], wherein the α,β-unsaturated carbonyl compound is an α,β-unsaturated ketones having from 5 to 18 carbon atoms.

As described in the foregoing, as the catalyst of the asymmetric hydrogenation reaction, the invention uses an optically active peptide compound as additives which contribute to the enantio-selectivity, together with a metal powder or metal-supported substance and an acid.

The asymmetric hydrogenation catalyst of the invention does not require a reaction step for preparing a catalyst like the conventional asymmetric hydrogenation catalyst. In the invention, asymmetric hydrogenation is carried out by simply mixing a raw material compound, an optically active peptide compound, a metal powder or metal-supported substance and an acid. Thus, the operation is convenient and the metal powder or metal-supported substance and optically active peptide compound can be recovered and reused, which is industrially advantageous.

In addition, in the case of using, as a substance, each of a Z-configuration or E-configuration compound regarding the double bond at the α-position and β-position of the α,β-unsaturated carbonyl compound, when using the catalyst of the invention, the configuration of the formed optically active carbonyl compound depends on the configuration of the optically active peptide compound to be used. Thus, according to the invention, even when a mixture of the Z-configuration compound and E-configuration compound is used as the substrate, an optically active carbonyl compound having the same configuration can be produced.

DETAILED DESCRIPTION OF THE INVENTION

The following describes the invention in detail.
Herein, "% by weight" and "part by weight" have the same meanings as "% by mass" and "part by mass" respectively.
<Catalyst>
According to the invention, an α,β-unsaturated carbonyl compound is used as the substrate, and an optically active aldehyde or an optically active ketone, which is an optically active carbonyl compound, is produced by subjecting this to asymmetric hydrogenation using the catalyst of the invention. First, the catalyst of the invention is described.
(Metal)
The catalyst of the invention is a catalyst for asymmetric hydrogenation of an α,β-unsaturated carbonyl compound, which comprises a powder of at least one metal selected from metals belonging to Group 8 to Group 10 of the Periodic Table, or a metal-supported substance in which at least one metal selected from metals belonging to Group 8 to Group 10 of the Periodic Table is supported on a support, an optically active peptide compound represented by the general formula (1), and an acid.

The following describes the powder of at least one metal selected from metals belonging to Group 8 to Group 10 of the Periodic Table and the metal-supported substance in which at least one metal selected from metals belonging to Group 8 to Group 10 of the Periodic Table is supported on a support.

As the metals belonging to Group 8 to Group 10 of the Periodic Table, Ni (nickel), Ru (ruthenium), Rh (rhodium), Ir (iridium), Pd (palladium) and Pt (platinum) are desirable, of which particularly desirable metal is Pd.

As the metal powder, Pd black, Pt black, Raney nickel and the like can, for example, be mentioned.

As the metal-supported substance, those in which the above-mentioned metals are supported on a support are used, and those in which these metals are supported on supports such as carbon, silica, alumina, silica-alumina, zeolite, a metal oxide, a metal halide, a metal sulfide, a metal sulfonate, a metal nitrate, a metal carbonate or a metal phosphate are suitably used. Among these, a substance in which palladium or platinum is supported on a support is desirable.

As illustrative metal-supported substance, Ru/C, Rh/C, Pd/C, Ir/C, Pt/C, Pd/C(en)(palladium/carbon-ethylenediamine complex), Pd/Fib(palladium-fibroin), Pd/PEI(palladium-polyethyleneimine), $Pd/Al_2O_3$, $Pd/SiO_2$, $Pd/TiO_2$, $Pd/ZrO_2$, $Pd/CeO_2$, $Pd/ZnO$, $Pd/CdO$, $Pd/TiO_2$, $Pd/SnO_2$, $Pd/PbO$, $Pd/As_2O_3$, $Pd/Bi_2O_3$, $Pd/Sb_2O_5$, $Pd/V_2O_5$, $Pd/Nb_2O_5$, $Pd/Cr_2O_3$, $Pd/MoO_3$, $Pd/WO_3$, $Pd/BeO$, $Pd/MgO$, $Pd/CaO$, $Pd/SrO$, $Pd/BaO$, $Pd/Y_2O_3$, $Pd/La_2O_3$, $Pd/Na_2O$, $Pd/K_2O$, $Pd/CdS$, $Pd/ZnS$, $Pd/MgSO_4$, $Pd/CaSO_4$, $Pd/SrSO_4$, $Pd/BaSO_4$, $Pd/CuSO_4$, $Pd/ZnSO_4$, $Pd/CdSO_4$, $Pd/Al_2(SO_4)_3$, $Pd/FeSO_4$, $Pd/Fe_2(SO_4)_3$, $Pd/CoSO_4$, $Pd/NiSO_4$, $Pd/Cr_2(SO_4)_3$, $Pd/KHSO_4$, $Pd/K_2SO_4$, $Pd/(NH_4)_2SO_4$, $Pd/Zn(NO_3)_2$, $Pd/Ca(NO_3)_2$, $Pd/Bi(NO_3)_3$, $Pd/Fe(NO_3)_3$, $Pd/Na_2CO_3$, $Pd/K_2CO_3$, $Pd/KHCO_3$, $Pd/KNaCO_3$, $Pd/CaCO_3$, $Pd/SrCO_3$, $PdIBaCO_3$, $Pd/(NH_4)_2CO_3$, $Pd/Na_2WO_4.2H_2O$, $Pd/KCN$, $Pd/BPO_4$, $Pd/AlPO_4$, $Pd/CrPO_4$, $Pd/FePO_4$, $Pd/Cu_3(PO_4)_2$, $Pd/Zn_3(PO_4)_2$, $Pd/Mg_3(PO_4)_2$, $Pd/Ti_3(PO_4)_4$, $Pd/Zr_3(PO_4)_4$, $Pd/Ni_3(PO_4)_2$, $Pd/AgCl$, $Pd/CuCl$, $Pd/CaCl_2$, $Pd/AlCl_3$, $Pd/TiCl_3$, $Pd/SnCl_2$, $Pd/CaF_2$, $Pd/BaF_2$, $Pd/AgClO_4$, $Pd/Mg(ClO_4)_2$, $Pd/Zeolite$, $Pd/SiO_2$—$Al_2O_3$, $Pd/SiO_2$—$TiO_3$, $Pd/SiO_2$—$ZrO_2$, $Pd/SiO_2$—$BeO$, $Pd/SiO_2$—$MgO$, $Pd/SiO_2$—$CaO$, $Pd/SiO_2$—$SrO$, $Pd/SiO_2$—$BaO$, $Pd/SiO_2$—$ZnO$, $Pd/SiO_2$—$TiO_2$, $Pd/SiO_2$—$ZrO_2$, $Pd/SiO_2$—$Ga_2O_3$, $Pd/SiO_2$—$Y_2O_3$, $Pd/SiO_2$—$La_2O_3$, $Pd/SiO_2$—$MoO_3$, $Pd/SiO_2$—$WO_3$, $Pd/SiO_2$—$V_2O_5$, $Pd/SiO_2$—$ThO_2$, $Pd/Al_2O_3$—$MgO$, $Pd/Al_2O_3$—$ZnO$, $Pd/Al_2O_3$—$CdO$, $Pd/Al_2O_3$—$B_2O_3$, $Pd/Al_2O_3$—$ThO_2$, $Pd/Al_2O_3$—$TiO_2$, $Pd/Al_2O_3$—$ZrO_2$, $Pd/Al_2O_3$—$V_2O_5$, $Pd/Al_2O_3$—$MoO_3$, $Pd/Al_2O_3$—$WO_3$, $PdIAl_2O_3$—$Cr_2O_3$, $Pd/Al_2O_3$—$Mn_2O_3$, $Pd/Al_2O_3$—$Fe_2O_3$, $Pd/Al_2O_3$—$CO_3O_4$, $Pd/Al_2O_3$—$NiO$, $Pd/TiO_2$—$CuO$, $Pd/TiO_2$—$MgO$, $Pd/TiO_2$—$ZnO$, $Pd/TiO_2$—$CdO$, $Pd/TiO_2$—$ZrO_2$, $Pd/TiO_2$—$SnO_2$, $PdITiO_2$—$Bi_2O_3$, $Pd/TiO_2$—$Sb_2O_5$, $Pd/TiO_2$—$V_2O_5$, $Pd/TiO_2$—$Cr_2O_3$, $Pd/TiO_2$—$MoO_3$, $Pd/TiO_2$—$WO_3$, $Pd/TiO_2$—$Mn_2O_3$, $Pd/TiO_2$—$Fe_2O_3$, $Pd/TiO_2$—$CO_3O_4$, $Pd/TiO_2$—$NiO$, $Pd/ZrO_2$—$CdO$, $Pd/ZnO$—$MgO$, $Pd/ZnO$—$Fe_2O_3$, $Pd/MoO_3$—$CoO$—$Al_2O_3$, $Pd/MoO_3$—$NiO$—$Al_2O_3$, $Pd/TiO_2$—$SiO_2$—$MgO$, $Pd/MoO_3$—$Al_2O_3$—$MgO$, $Pd/Heteropoly$ acids, $Pt/SiO_2$, $Pt/Al_2O_3$, $Pt/Zeolite$, $Rh/Al_2O_3$ and the like can be mentioned.

(Optically Active Peptide Compound)

Subsequently, an optically active peptide compound used as the catalyst component of the present invention and represented by the general formula (1) is described.

[Chem. 4]

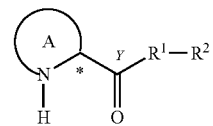

(1)

In the formula (1), ring A is a 3- to 7-membered ring which may have a substituent group, contains at least one atom selected from the group consisting of a carbon atom, a nitrogen atom, a sulfur atom, an oxygen atom and a phosphorus atom, and may be a fused ring structure. $R^1$ represents an amino acid residue which is bonded to a carbonyl group at Y-position by a peptide bond or a peptide residue which is constituted from 2 to 30 amino acids and is bonded to a carbonyl group at Y-position by a peptide bond. $R^2$ represents an amino group which is bonded to a carbonyl group at C-terminus of $R^1$, an alkoxy group which is bonded to a carbonyl group at C-terminus of $R^1$, a hydroxy group which is bonded to a carbonyl group at C-terminus of $R^1$ or a polymer chain which is bonded to a carbonyl group at C-terminus of $R^1$, and * represents an asymmetric carbon atom.

The amino acid constituting a unit of the amino acid residue or the peptide residue as $R^1$ of the optically active peptide compound represented by the general formula (1) is described. As the amino acid, examples thereof include, as an amino acid which is not optically active, glycine, 2,2-dimethylglycine and the like, and examples thereof include, as an optically active amino acid, alanine, valine, leucine, isoleucine, phenylalanine, proline, tryptophan, tyrosine, histidine, arginine, asparagine, asparagine acid, cysteine, glutamine, glutamine acid, lysine, methionine, serine, threonine and the like, which are D-, L-, and DL-amino acids.

$R^2$, as the terminus of the optically active peptide compound, represents an amino group, an alkoxy group, a hydroxy group, or a polymer chain.

As the amino group of $R^2$, an amino group having, for example, from 1 to 20 carbon atoms is desirable, and illustrative examples thereof include mono- or di-alkylamino groups such as N-methylamino group, N,N-dimethylamino group, N,N-diethylamino group, N,N-diisopropylamino group, N-cyclohexylamino group, pyrrolidyl group, piperidyl group and morpholyl group; mono- or di-arylamino group such as N-phenylamino group, N,N-diphenylamino group, N-naphthylamino group and N-naphthyl-N-phenylamino group; mono- or di-aralkylamino group such as N-benzylamino group, N,N-dibenzylamino group and 1-phenylethylamino group; and the like.

As the alkoxy group of $R^2$, an alkoxy group having, for example, from 1 to 30 carbon atoms is desirable, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group, dicyclopentylmethoxy group, dicyclohexylmethoxy group, tricyclopentyl methoxy group, tricyclohexylmethoxy group, phenylmethoxy group, diphenylmethoxy group, triphenylmethoxy group and the like.

As the polymer chain of $R^2$, examples thereof include polystyrene bonded to $R^1$ as an alkoxy group, polystyrene bonded to $R^1$ as an amino group, and the like.

As $R^2$, among these, an amino group is desirable, and particularly, N-phenylamino group and 1-phenylethylamino group are desirable.

As basic skeleton of the ring A, examples thereof include aziridine skeleton, azetidine skeleton, pyrrolidine skeleton, pyrroline skeleton, pyrazolidine skeleton, imidazolidine skeleton, imidazolidinone skeleton, pyrazoline skeleton, thiazolidine skeleton, piperidine skeleton, piperazine skeleton, morpholine skeleton, thiomorpholine skeleton and the like. A substituent group may be present in these basic skeletons.

As the basic skeleton in the case where the ring A is a fused ring structure by benzene ring or the like, examples thereof include indoline skeleton, dihydroquinoxaline skeleton, tetrahydroisoquinoline skeleton, dihydroquinoxalinone skeleton and the like. A substituent group may be present in these basic skeletons.

As the ring A and fused ring A, among these, pyrrolidine skeleton which may have a substituent group and piperidine skeleton which may have a substituent group are desirable.

As the substituent group of the ring A and fused ring A, examples thereof include an oxo group, a halogen atom, an acyl group, an alkyl group which may have a substituent group, a cycloalkyl group which may have a substituent group, a hydroxyl group, an alkoxy group which may have a substituent group, an alkenyl group which may have a substituent group, an aryl group which may have a substituent group, an aralkyl group which may have a substituent group, an amino group which may have a substituent group, an alkoxycarbonyl group which may have a substituent group, an amido group which may have a substituent group, an aromatic heterocyclic group which may have a substituent group, and an aliphatic heterocyclic group which may have a substituent group.

As the halogen atom, examples thereof include fluorine atom, chlorine atom, bromine atom, iodine atom and the like.

As the acyl group, examples thereof include acetyl group, propanoyl group, butanoyl group, octanoyl group, benzoyl group, toluoyl group, xyloyl group, naphthoyl group, phenanthroyl group, anthroyl group and the like.

As the alkyl group, a chain or branched alkyl group having, for example, from 1 to 30 carbon atoms, preferably from 1 to 10 carbon atoms, can be mentioned, and illustrative examples thereof include a methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group and the like.

In addition, these alkyl groups may have a substituent group, and as the substituent group of alkyl groups, examples thereof include an alkenyl group, an alkynyl group, an aryl group, an aliphatic heterocyclic group, an aromatic heterocyclic group, an alkoxy group, a trialkylsiloxy group, an alkylenedioxy group, an aryloxy group, an aralkyloxy group, a heteroaryloxy group, a substituted amino group, an alkyl halide group, a cycloalkyl group, a hydroxyl group, an amino group, a halogen atom and the like.

As the alkenyl group as the substituent group of the alkyl group, examples thereof include a straight chain or branched alkenyl group having, for example, from 2 to 20 carbon atoms, preferably from 2 to 10 carbon atoms, more preferably from 2 to 6 carbon atoms, and illustrative examples thereof include vinyl group, propenyl group, 1-butenyl group, pentenyl group, hexenyl group and the like.

As the alkynyl group as the substituent group of the alkyl group, examples thereof include a straight chain or branched alkynyl group having, for example, from 2 to 15 carbon atoms, preferably from 2 to 10 carbon atoms, more preferably from 2 to 6 carbon atoms, and illustrative examples thereof include ethynyl group, 1-propynyl group, 2-propynyl group, 1-butynyl group, 3-butynyl group, pentinyl group, hexynyl group and the like.

As the aryl group as the substituent group of the alkyl group, an aryl group having, for example, from 6 to 20 carbon atoms can be mentioned, and illustrative examples thereof include phenyl group, tolyl group, isopropylphenyl group, xylyl group, t-butylphenyl group, adamantylphenyl group, trifluoromethylphenyl group, naphthyl group, anthryl group, phenanthryl group, biphenyl group, 4-(2'-p-tolylpropyl)phenyl group, mesityl group, methoxyphenyl group, dimethoxyphenyl group, 4-(3',4',5',6',7',8',9',10'-heptadecafluorodecyl)phenyl group, fluorophenyl group and the like.

As the aliphatic heterocyclic group as the substituent group of the alkyl group, examples thereof include a group which has, for example, 2 to 14 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, tetrahydrothienyl group and the like.

As the aromatic heterocyclic group as the substituent group of the alkyl group, examples thereof include a group which has, for example, 2 to 15 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As the aromatic heterocyclic group, illustrative examples thereof include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as the substituent group of the alkyl group, a straight chain or branched alkoxy group having, for example, from 1 to 8 carbon atoms can be mentioned, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group and the like.

As the trialkylsiloxy group as the substituent group of the alkyl group, examples thereof include trimethylsiloxy group, triethylsiloxy group, dimethyl-tert-butylsiloxy group and the like.

As the alkylenedioxy group as the substituent group of the alkyl group, an alkylenedioxy group having, for example, from 1 to 3 carbon atoms can be mentioned, and illustrative examples thereof include methylenedioxy group, ethylenedioxy group, propylenedioxy group, isopropylidenedioxy group and the like.

As the aryloxy group as the substituent group of the alkyl group, an aryloxy group having, for example, from 6 to 15 carbon atoms can be mentioned, and illustrative examples thereof include phenoxy group, naphthyloxy group, anthryloxy group, tolyloxy group, xylyloxy group, 4-phenylphenoxy group, 3,5-diphenylphenoxy group, 4-mesitylphenoxy group, 3,5-bis(trifluoromethyl)phenoxy group and the like.

As the aralkyloxy group as the substituent group of the alkyl group, an aralkyloxy group having, for example, from 7 to 12 carbon atoms can be mentioned, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

As the heteroaryloxy group as the substituent group of the alkyl group, examples thereof include a heteroaryloxy group which has, for example, 2 to 14 carbon atoms and contains, as heterogeneous atoms, at least one, preferably 1 to 3 hetero atoms such as nitrogen atom, oxygen atom and sulfur atom, and illustrative examples thereof include 2-pyridyloxy group, 2-pyrazyloxy group, 2-pyrimidyloxy group, 2-quinolyloxy group and the like.

As the substituted amino group as the substituent group of the alkyl group, examples thereof include mono- or di-alkylamino groups such as N-methylamino group, N,N-dimethylamino group, N,N-diethylamino group, N,N-diisopropylamino group, N-cyclohexylamino group, pyrrolidyl group, piperidyl group and morpholyl group; mono- or di-arylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group; and the like.

As the alkyl halide group as the substituent group of the alkyl group, a perhalogenoalkyl group is desirable, and examples thereof include trifluoromethyl group, pentafluoroethyl group, heptafluoropropyl group, undecafluoropentyl group, heptadecafluorooctyl group, undecafluorocyclohexyl group, dichloromethyl group and the like.

As the cycloalkyl group as the substituent group of the alkyl group, examples thereof include cyclopropyl group, cyclobutyl group, cyclopentyl group, cyclohexyl group, 1-methylcyclohexyl group and the like.

As the halogen atom as the substituent group of the alkyl group, examples thereof include fluorine atom, chlorine atom, bromine atom, iodine atom and the like.

As the cycloalkyl group, examples thereof include cyclopropyl group, cyclobutyl group, cyclopentyl group, cyclohexyl group, 1-methylcyclohexyl group and the like can be mentioned.

These cycloalkyl groups may have a substituent group, and as the substituent group, the substituent groups described in the aforementioned description on the substituent group of the alkyl group can be mentioned.

As the alkoxy group, an alkoxy group having, for example, from 1 to 30 carbon atoms is desirable, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group, dicyclopentylmethoxy group, dicyclohexylmethoxy group, tricyclopentyl methoxy group, tricyclohexylmethoxy group, phenylmethoxy group, diphenylmethoxy group, triphenylmethoxy group and the like.

These alkoxy groups may have a substituent group, and as the substituent group, the groups described in the description on the substituent group of the alkyl group can be mentioned.

As the alkenyl group, a chain or branched or cyclic alkenyl group having, for example, from 2 to 20 carbon atoms, preferably from 2 to 10 carbon atoms, can be mentioned. As illustrative alkenyl groups, examples thereof include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, 3-cyclohexenyl group and the like.

These alkenyl groups may have a substituent group, and as the substituent group, the groups described in the aforementioned description on the substituent group of the alkyl group can be mentioned.

As the aryl group, an aryl group having, for example, from 6 to 20 carbon atoms can be mentioned, and illustrative examples thereof include phenyl group, tolyl group, isopropylphenyl group, xylyl group, t-butylphenyl group, adamantylphenyl group, trifluoromethylphenyl group, naphthyl group, anthryl group, phenanthryl group, biphenyl group, 4-(2'-p-tolylpropyl)phenyl group, mesityl group, methoxyphenyl group, dimethoxyphenyl group, 4-(3',4',5',6',7',8',9', 10'-heptadecafluorodecyl)phenyl group, fluorophenyl group and the like.

These aryl groups may have a substituent group, and as the substituent group, the groups described in the description on the substituent group of the alkyl group can be mentioned.

As the aralkyl group, an aralkyl group having, for example, from 7 to 45 carbon atoms is desirable, and illustrative examples thereof include benzyl group, tolylmethyl group, xylylmethyl group, mesitylmethyl group, 4-phenylphenylmethyl group, 3-phenylphenylmethyl group, 2-phenylphenylmethyl group, 4-mesitylphenylmethyl group, 1-naphthylmethyl group, 2-naphthylmethyl group, 9-anthrylmethyl group, 9-phenanthrylmethyl group, 3,5-diphenylphenylmethyl group, 2-phenylethyl group, 1-phenylpropyl group, 3-naphthylpropyl group, diphenylmethyl group, ditolylmethyl group, dixylylmethyl group, dimesitylmethyl group, di(4-phenylphenyl)methyl group, di(3-phenylphenyl)methyl group, di(2-phenylphenyl)methyl group, di(4-mesitylphenyl)methyl group, di-1-naphthylmethyl group, di-2-naphthylmethyl group, di-9-anthrylmethyl group, di-9-phenanthrylmethyl group, bis(3,5-diphenylphenyl)methyl group, triphenylmethyl group, tritolylmethyl group, trixylylmethyl group, trimesitylmethyl group, tri(4-phenylphenyl)methyl group, tri(3-phenylphenyl)methyl group, tri(2-phenylphenyl) methyl group, tri(4-mesitylphenyl)methyl group, tri-1-naphthyl methyl group, tri-2-naphthylmethyl group, tri-9-anthrylmethyl group, tri-9-phenanthrylmethyl group, tris(3,5-diphenylphenyl)methyl group, trimethylsiloxyphenylmethyl group, trimethylsiloxydiphenyl methyl group, trimethylsiloxyditolyl methyl group, trimethyl siloxydi(4-t-butylphenyl)methyl group, trimethylsiloxydixylylmethyl group, trimethylsiloxydi(2-phenylphenyl)methyl group, trimethylsiloxydi(3-phenylphenyl)methyl group, trimethylsiloxydi(4-phenylphenyl)methyl group, trimethylsiloxybis(3,5-diphenylphenyl)methyl group, trimethylsiloxydi(4-mesitylphenyl)methyl group, trimethylsiloxybis(3,5-ditrifluoromethylphenyl)methyl group and the like.

These aralkyl groups may have a substituent group, and as the substituent group, the groups described in the description on the substituent group of the alkyl group can be mentioned.

As the amino group, an amino group having, for example, from 1 to 20 carbon atoms is desirable, and illustrative examples thereof include an amino group; mono- or di-alkylamino groups such as N-methylamino group, N,N-dimethylamino group, N,N-diethylamino group, N,N-diisopropylamino group, N-cyclohexylamino group, pyrrolidyl group, piperidyl group and morpholyl group; mono- or di-arylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group; and the like.

These amino groups may have a substituent group, and as the substituent group, the substituent groups described in the aforementioned description of the alkyl group can be mentioned.

As the alkoxycarbonyl group, an alkoxycarbonyl group having, for example, from 1 to 30 carbon atoms is desirable, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like.

These alkoxycarbonyl groups may have a substituent group, and as the substituent group, the groups described in the description on the substituent group of the alkyl group can be mentioned.

As the amido group, an amido group having, for example, from 1 to 30 carbon atoms is desirable, and illustrative examples thereof include acetamido group, n-propionamido group, isopropionamido group, n-butanamido group, 2-butanamido group, isobutanamido group, tert-butanamido group, n-pentanamido group, 2-methylbutanamido group, 3-methylbutanamido group, 2,2-dimethyl propionamido group, n-hexanamido group, 2-methylpentanamido group, 3-methylpentanamido group, 4-methylpentanamido group, 5-methylpentanamido group, cyclopentanamido group, cyclohexanamido group, dicyclopentylacetamido group, dicyclohexylacetamido group, tricyclopentylacetamido group, tricyclohexylacetamido group, phenylacetamido group, diphenylacetamido group, triphenylacetamido group, benzamido group, naphthalenamido group and the like.

These amido groups may have a substituent group, and as the substituent group, the groups described in the description on the substituent group of the alkyl group can be mentioned.

As the aromatic heterocyclic group, examples thereof include a group which has, for example, from 2 to 15 carbon atoms and contains, as heterogeneous atoms, at least one, preferably from 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As illustrative examples of the aromatic heterocyclic group, examples thereof include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

These aromatic heterocyclic groups may have a substituent group, and as the substituent group, the groups described in the description on the substituent group of the alkyl group can be mentioned.

As the aliphatic heterocyclic group, examples thereof include a group which has, for example, from 2 to 14 carbon atoms and contains, as heterogeneous atoms, at least one, preferably from 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, tetrahydrothienyl group and the like.

These aliphatic heterocyclic groups may have a substituent group, and as the substituent group, the groups described in the description on the substituent group of the alkyl group can be mentioned.

As illustrative examples of the optically active peptide compound represented by the general formula (1), the following compounds can, for example, be mentioned.

In the following compounds, polymer represents polymer chain, and D-Pro represents D-proline residue, Pro represents L-proline residue, D-Pic represents D-Pipecolinic Acid, and Pic represents L-Pipecolinic Acid.

[Chem. 5]

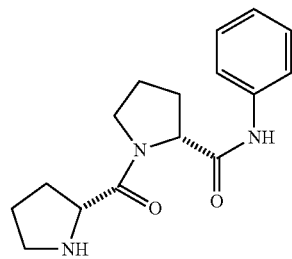

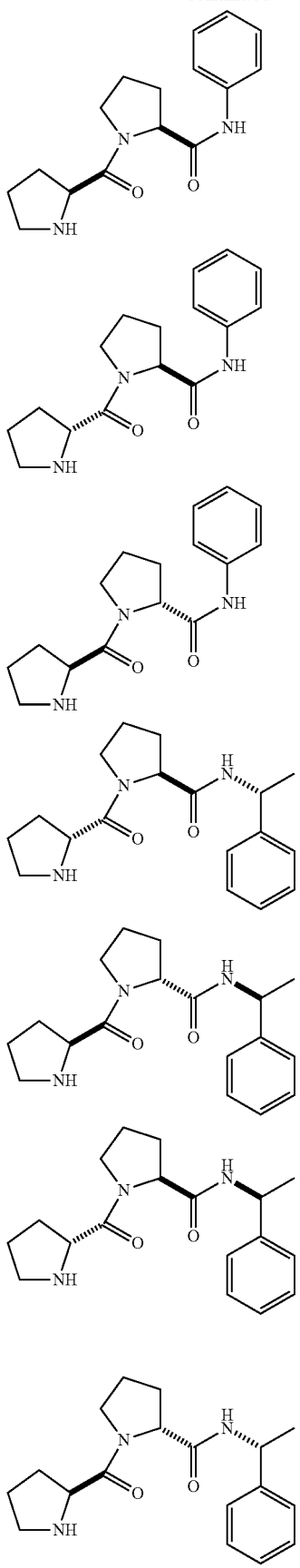
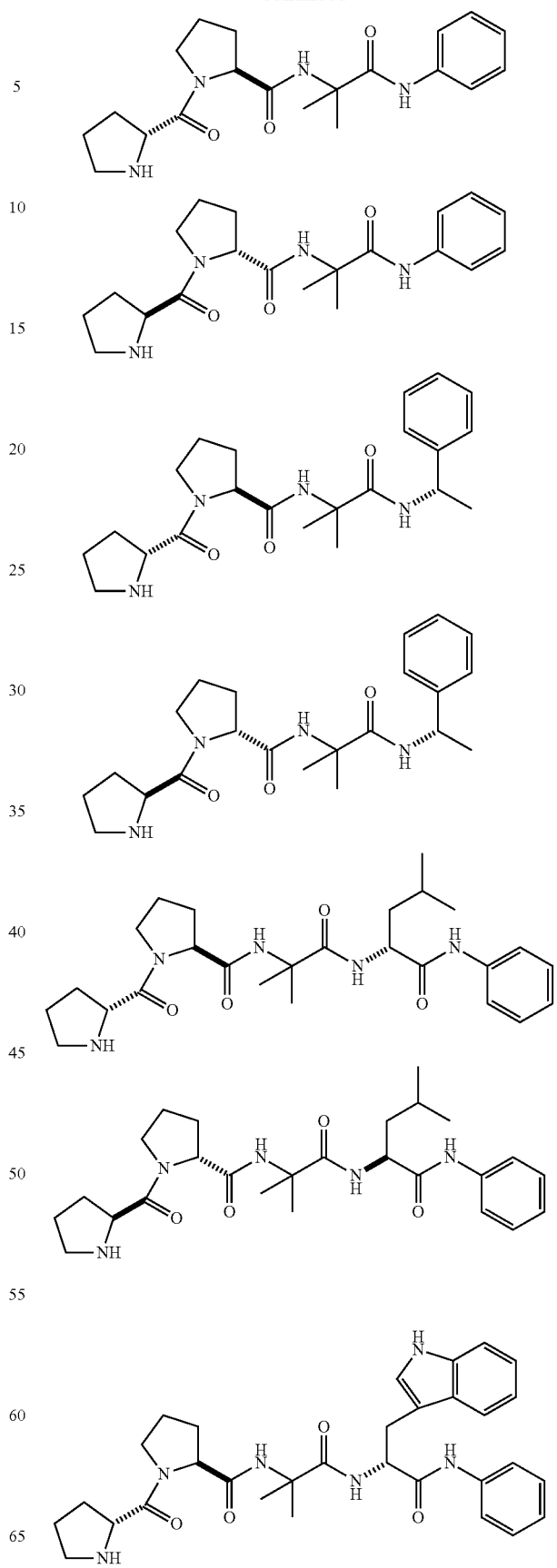

[Chem. 6]

[Chem. 7]

H-D-Pro-(amino acid)$_{1-30}$-polymer

H-Pro-(amino acid)$_{1-30}$-polymer

H-D-Pic-(amino acid)$_{1-30}$-polymer

H-Pic-(amino acid)$_{1-30}$-polymer

The optically active peptide compound represented by the general formula (1) can be synthesized by a general peptide synthesis method. The synthesis method may be represented by, for example, the following Schemes 1 to 11.

In the Schemes, HO-Su, HO-Bt, Boc and EDCl represent the followings, respectively.

[Chem. 8]

EDCl = H$_3$CH$_2$CN=C=N(CH$_2$)$_3$N(CH$_3$)$_2$·HCl

In the Schemes,
Pro represents L-proline residue,
D-Pro represents D-proline residue,
Leu represents L-leucine residue,
Aib represents 2,2-dimethylglycine residue,
Trp represents L-tryptophan residue,
Phe represents L-phenylalanine residue,
Gly represents glycine residue.

In the Schemes, Bn represents benzyl group, and Ph represents phenyl group.

Scheme 4
[Chem. 10]
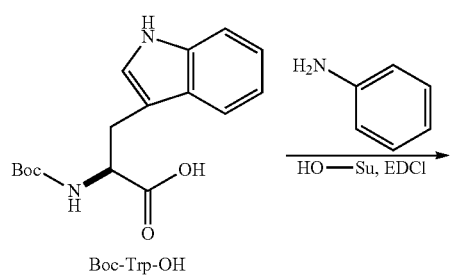
Boc-Trp-OH
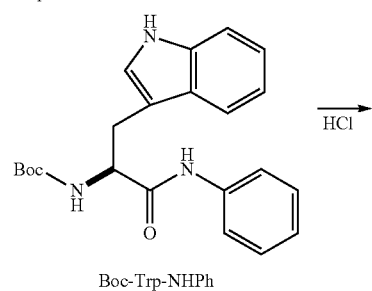
Boc-Trp-NHPh
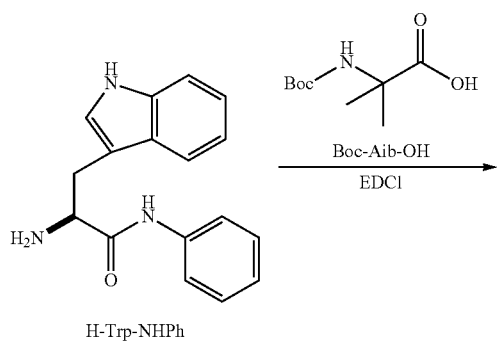
H-Trp-NHPh
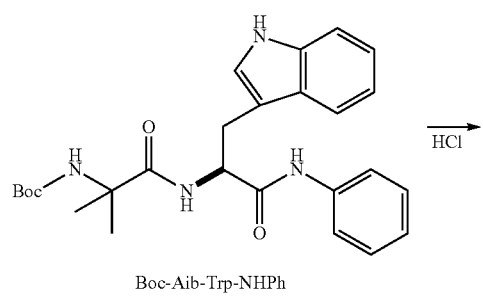
Boc-Aib-Trp-NHPh
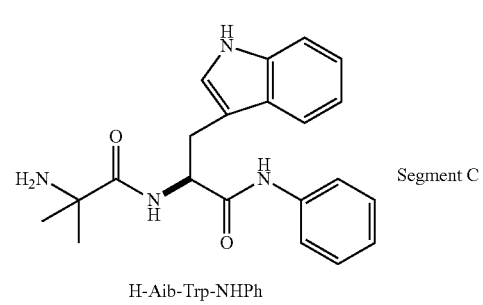
H-Aib-Trp-NHPh
Scheme 5
Segment A + Segment C →(HO—Bt, EDCl)
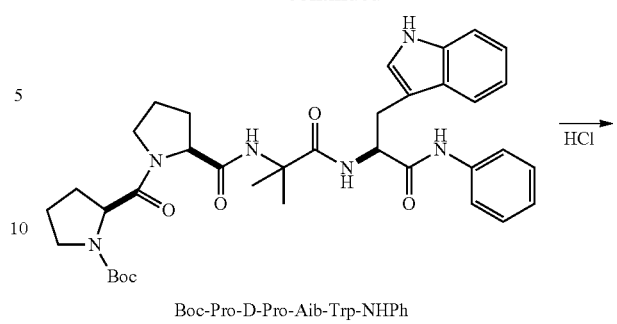
Boc-Pro-D-Pro-Aib-Trp-NHPh
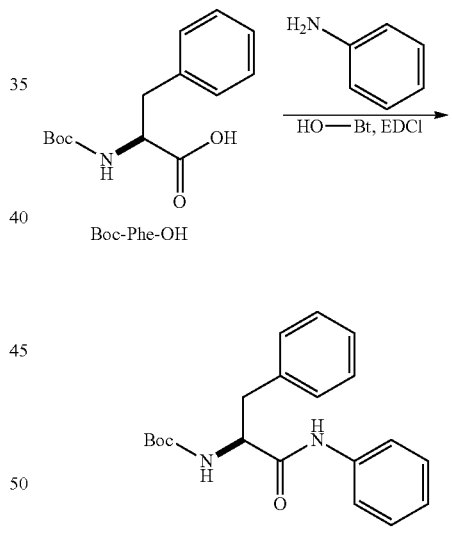
H-Pro-D-Pro-Aib-Trp-NHPh
Scheme 6
[Chem. 11]
Boc-Phe-OH →(HO—Bt, EDCl, H₂N-Ph)
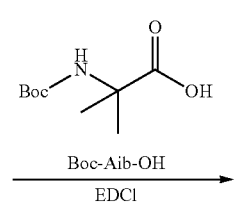
Boc-Phe-NHPh →HCl
H-Phe-NHPh →(Boc-Aib-OH, EDCl)

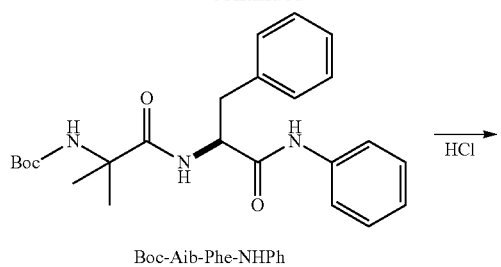
Boc-Aib-Phe-NHPh
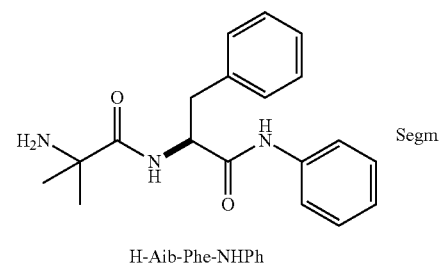
Segment D
H-Aib-Phe-NHPh
Scheme 7
Segment A + Segment D →(HO-Bt, EDCl)
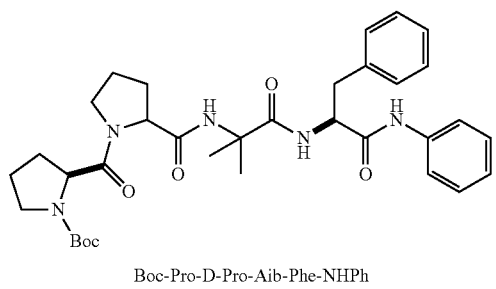
Boc-Pro-D-Pro-Aib-Phe-NHPh
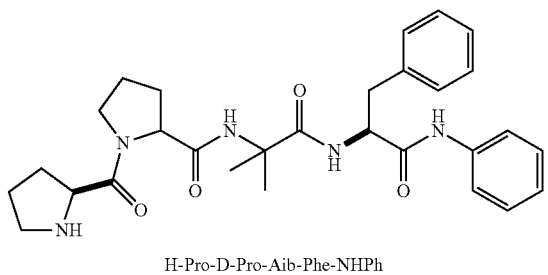
H-Pro-D-Pro-Aib-Phe-NHPh
Scheme 8
[Chem. 12]
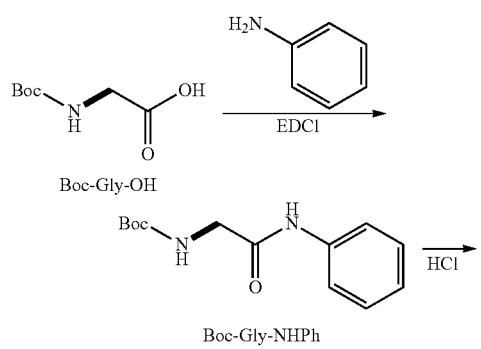
Boc-Gly-NHPh
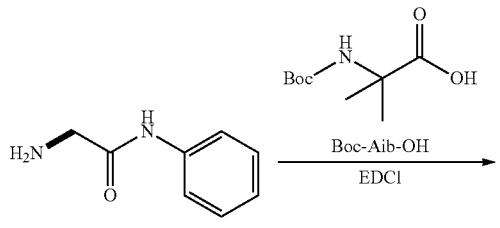
H-Gly-NHPh →(Boc-Aib-OH, EDCl)
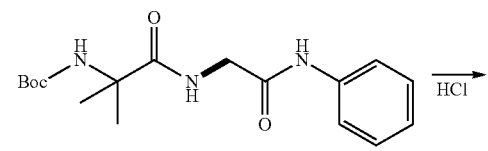
Boc-Aib-Gly-NHPh
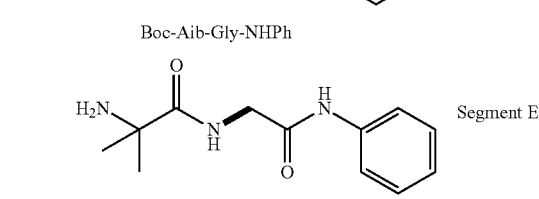
Segment E
H-Aib-Gly-NHPh
Scheme 9
Segment A + Segment E →(HO—Bt, EDCl)
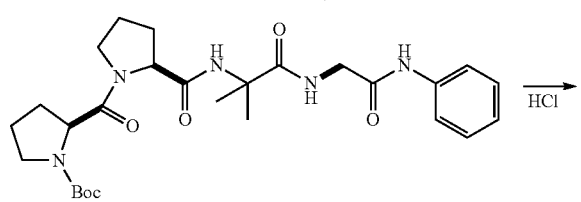
Boc-Pro-D-Pro-Aib-Gly-NHPh
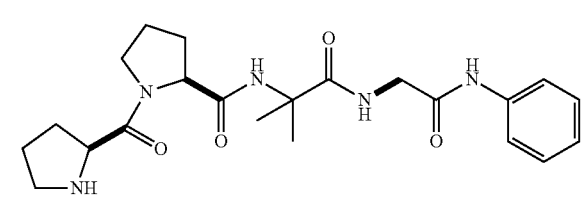
H-Pro-D-Pro-Aib-Gly-NHPh
Scheme 10
[Chem. 13]
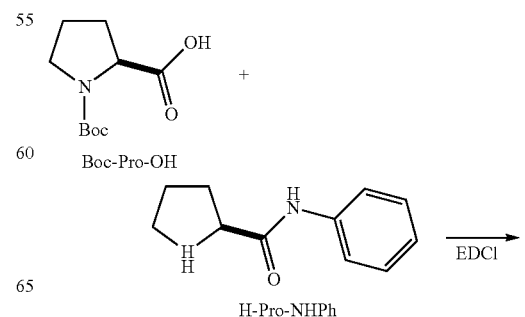
H-Pro-NHPh →(EDCl)

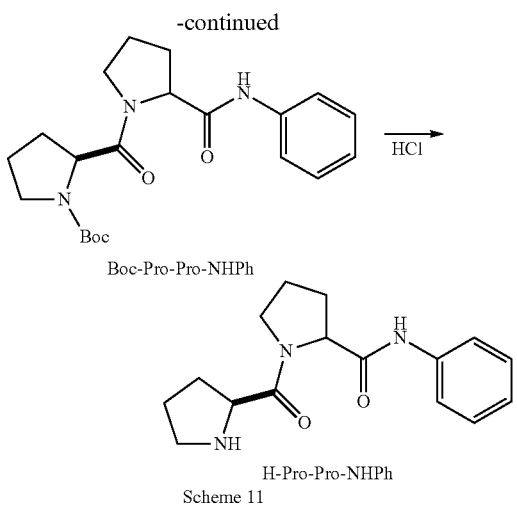

Boc-Pro-Pro-NHPh

H-Pro-Pro-NHPh

Scheme 11

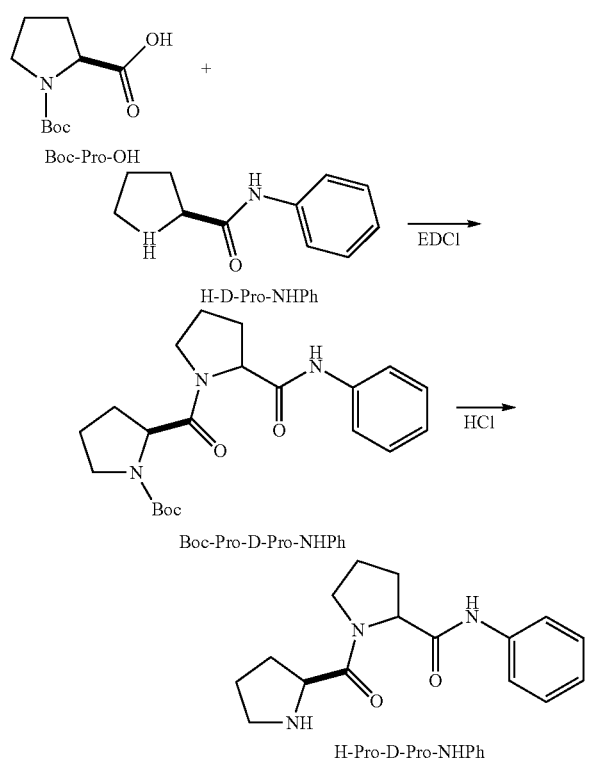

Boc-Pro-OH

H-D-Pro-NHPh

Boc-Pro-D-Pro-NHPh

H-Pro-D-Pro-NHPh

In the above-mentioned method, an amino acid protected by Boc or the like and an amino acid with the terminus protected by amine or the like is subjected to dehydration in a solvent such as DMF(N,N-dimethylformamide) and THF (tetrahydrofuran) using a dehydrating agent such as EDCl(N-ethyl-N'-(3-dimethylaminopropyl)carbodiimide hydrochloride) and DCC(dicyclohexy carbodiimide), thereby producing a peptide bond. Then, Boc or the like serving as a protecting group is removed by acid such as hydrochloric acid, thereby obtaining peptide. By repeating the operation, it is possible to obtain a desired peptide compound.

(Acid)

In addition, according to the invention, an acid is included as another catalyst component.

As the acid, an organic acid or an inorganic acid can be used, but an organic acid is desirable.

As the organic acid, illustrative examples thereof include acetic acid, chloroacetic acid, difluoroacetic acid, trifluoroacetic acid, trichloroacetic acid, tribromoacetic acid, benzoic acid, 2,4-dinitrobenzoic acid, paratoluenesulfonic acid, methanesulfonic acid, L-lactic acid, DL-tropic acid, DL-malic acid, L-malic acid, D-malic acid, DL-tartaric acid, D-tartaric acid, L-tartaric acid, L-dibenzoyltartaric acid, D-dibenzoyltartaric acid, DL-mandelic acid, L-mandelic acid, D-mandelic acid, trifluoromethanesulfonic acid, and the like.

As the inorganic acid, illustrative examples thereof include hydrofluoric acid, hydrochloric acid, bromic acid, iodic acid, sulfuric acid, perchloric acid, phosphoric acid, nitric acid and the like.

<Substrate>

According to the invention, an α,β-unsaturated carbonyl compound is used as the substrate, and an optically active aldehyde or an optically active ketone, which is an optically active carbonyl compound, is produced by subjecting this to asymmetric hydrogenation using the catalyst of the invention.

As the α,β-unsaturated carbonyl compound to be used as the substrate, a compound represented by the following general formula (2) can, for example, be mentioned, though not particularly limited thereto. In this connection, in the case of the presence of Z-configuration and E-configuration regarding the double bond at the α-position and β-position of the α,β-unsaturated carbonyl compound, all of them are included therein.

General formula (2)

[Chem. 14]

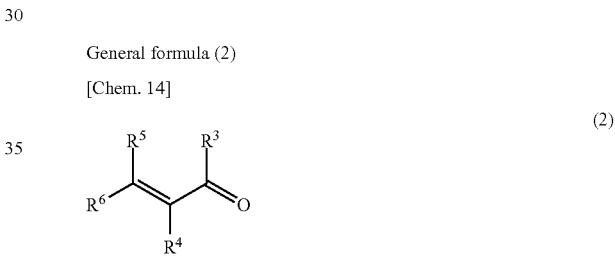

(2)

(In the formula (2), $R^3$, $R^4$, $R^5$ and $R^6$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, an alkoxycarbonyl group which may have a substituent group or an aralkyloxy group which may have a substituent group. In addition, $R^3$ and $R^4$, $R^3$ and $R^5$, $R^3$ and $R^6$, $R^4$ and $R^6$ or $R^5$ and $R^6$ may form a ring. However, when a ring is not formed by $R^3$ and $R^4$ or $R^3$ and $R^5$, and $R^4$ does not represent a hydrogen atom, $R^5$ and $R^6$ may be the same or different from each other; and when a ring is not formed by $R^3$ and $R^4$ or $R^3$ and $R^5$, and $R^4$ represents a hydrogen atom, $R^5$ and $R^6$ do not represent a hydrogen atom and are different from each other.)

An optically active aldehyde or an optically active ketone, which is an optically active carbonyl compound represented by the following formula (3), is produced by subjecting a compound represented by the aforementioned formula (2), namely an α,β-unsaturated aldehyde or an α,β-unsaturated ketone, to asymmetric hydrogenation using the catalyst of the invention.

[Chem. 15]

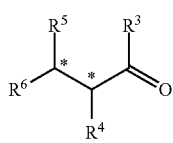

(3)

In the formula (3), $R^3$, $R^4$, $R^5$ and $R^6$ are the same as the definition of the formula (2). Two * mean that at least one * represents an asymmetric carbon atom.

Regarding the α,β-unsaturated carbonyl compound represented by the general formula (2) and the optically active carbonyl compound represented by the general formula (3), the groups represented by $R^3$, $R^4$, $R^5$ and $R^6$, namely the alkyl group, cycloalkyl group, alkenyl group, aryl group, aralkyl group, aromatic heterocyclic group, aliphatic heterocyclic group, acyl group, alkoxycarbonyl group and aralkyloxy group, are described. Each of these groups may have a substituent group.

As the alkyl group, a chain or branched alkyl group having, for example, from 1 to 30 carbon atoms, preferably from 1 to 10 carbon atoms, can be mentioned, and illustrative examples thereof include methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group and the like.

In addition, these alkyl groups may have a substituent group, and as the substituent group of alkyl groups, examples thereof include an alkenyl group, an alkynyl group, an aryl group, an aliphatic heterocyclic group, an aromatic heterocyclic group, an alkoxy group, an alkylenedioxy group, an aryloxy group, an aralkyloxy group, a heteroaryloxy group, an amino group, a substituted amino group, a nitro group, a cyano group, an alkoxycarbonyl group, a halogen atom, an alkyl halide group and the like.

As the alkenyl group as the substituent group of the alkyl group, examples thereof include a straight chain or branched alkenyl group having, for example, from 2 to 20 carbon atoms, preferably from 2 to 10 carbon atoms, more preferably from 2 to 6 carbon atoms, and illustrative examples thereof include vinyl group, propenyl group, 1-butenyl group, pentenyl group, hexenyl group and the like.

As the alkynyl group as the substituent group of the alkyl group, examples thereof include a straight chain or branched alkynyl group having, for example, from 2 to 15 carbon atoms, preferably from 2 to 10 carbon atoms, more preferably from 2 to 6 carbon atoms, and illustrative examples thereof include ethynyl group, 1-propynyl group, 2-propynyl group, 1-butynyl group, 3-butynyl group, pentinyl group, hexynyl group and the like.

As the aryl group as the substituent group of the alkyl group, an aryl group having, for example, from 6 to 14 carbon atoms can be mentioned, and illustrative examples thereof include phenyl group, naphthyl group, anthryl group, phenanthryl group, biphenyl group, tolyl group, xylyl group, mesityl group, methoxyphenyl group, dimethoxyphenyl group, fluorophenyl group and the like.

As the aliphatic heterocyclic group as the substituent group of the alkyl group, examples thereof include a group which has, for example, from 2 to 14 carbon atoms and contains, as heterogeneous atoms, at least one, preferably from 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, tetrahydrothienyl group and the like.

As the aromatic heterocyclic group as the substituent group of the alkyl group, examples thereof include a group which has, for example, from 2 to 15 carbon atoms and contains, heterogeneous atoms, at least one, preferably from 1 to 3 hetero atoms such as nitrogen atom, oxygen atom and sulfur atom. Preferabe examples thereof include a 5- or 6-membered monocyclic aromatic heterocyclic group and a polycyclic or condensed ring aromatic heterocyclic group. As the aromatic heterocyclic group, illustrative examples thereof include furyl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as the substituent group of the alkyl group, a straight chain or branched alkoxy group having, for example, from 1 to 6 carbon atoms can be mentioned, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group and the like.

As the alkylenedioxy group as the substituent group of the alkyl group, an alkylenedioxy group having, for example, from 1 to 3 carbon atoms can be mentioned, illustrative examples thereof include methylenedioxy group, ethylenedioxy group, propylenedioxy group, isopropylidenedioxy group and the like.

As the aryloxy group as the substituent group of the alkyl group, an aryloxy group having, for example, from 6 to 14 carbon atoms can be mentioned, and illustrative examples thereof include phenoxy group, naphthyloxy group, anthryloxy group and the like.

As the aralkyloxy group as the substituent group of the alkyl group, for example, an aralkyloxy group having from 7 to 12 carbon atoms can be mentioned, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

As the heteroaryloxy group as the substituent group of the alkyl group, examples thereof include a heteroaryloxy group which has, for example, from 2 to 14 carbon atoms and contains, as heterogeneous atoms, at least one, preferably from 1 to 3 hetero atoms such as nitrogen atom, oxygen atom and sulfur atom, and illustrative examples thereof include 2-pyridyloxy group, 2-pyrazyloxy group, 2-pyrimidyloxy group, 2-quinolyloxy group and the like.

As the substituted amino group as the substituent group of the alkyl group, examples thereof include mono- or di-alkylamino groups such as N-methylamino group, N,N-dimethylamino group, N,N-diethylamino group, N,N-diisopropylamino group and N-cyclohexylamino group; mono- or di-arylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group; and the like.

As the alkoxycarbonyl group as the substituent group of the alkyl group, an alkoxycarbonyl group having, for example, from 1 to 30 carbon atoms is desirable, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like.

As the halogen atom as the substituent group of the alkyl group, for example, fluorine atom, chlorine atom, bromine atom, iodine atom and the like can be mentioned.

As the alkyl halide group as the substituent group of the alkyl group, a perhalogenoalkyl group is desirable, and examples thereof include trifluoromethyl group, pentafluoroethyl group, heptafluoropropyl group, undecafluoropentyl group, heptadecafluorooctyl group, undecafluorocyclohexyl group, dichloromethyl group and the like.

As the cycloalkyl group, for example, cyclopropyl group, cyclobutyl group, cyclopentyl group, cyclohexyl group and the like can be mentioned.

These cycloalkyl groups may have a substituent group, and as the substituent group, the substituent groups described in the aforementioned description on the substituent group of the alkyl group can be mentioned.

As the alkenyl group, a chain or branched or cyclic alkenyl group having, for example, from 2 to 20 carbon atoms, preferably from 2 to 10 carbon atoms, can be mentioned. As illustrative alkenyl groups, examples thereof include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, 3-cyclohexenyl group and the like.

These alkenyl groups may have a substituent group, and as the substituent group, the groups described in the aforementioned description on the substituent group of the alkyl group can be mentioned.

As the aryl group, an aryl group having, for example, from 6 to 14 carbon atoms can be mentioned, and illustrative examples thereof include phenyl group, naphthyl group, anthryl group, phenanthryl group, biphenyl group and the like.

These aryl groups may have a substituent group, and as the substituent group, the groups described in the description on the substituent group of the alkyl group can be mentioned.

As the aralkyl group, an aralkyl group having, for example, from 7 to 12 carbon atoms is desirable, and illustrative examples thereof include benzyl group, 2-phenylethyl group, 1-phenylpropyl group, 3-naphthylpropyl group and the like.

These aralkyl groups may have a substituent group, and as the substituent group, the groups described in the description on the substituent group of the alkyl group can be mentioned.

As the aromatic heterocyclic group, examples thereof include a group which has, for example, 2 to 15 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aromatic heterocyclic group and a polycyclic or condensed ring aromatic heterocyclic group. As the aromatic heterocyclic group, illustrative examples thereof include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

These aromatic heterocyclic groups may have a substituent group, and as the substituent group, the groups described in the description on the substituent group of the alkyl group can be mentioned.

As the aliphatic heterocyclic group, examples thereof include a group which has, for example, 2 to 14 carbon atoms and contains, as heterogeneous atoms, at least one, preferably 1 to 3 hetero atoms such as nitrogen atom, oxygen atom and sulfur atom. Preferable examples thereof include a 5- or 6-membered monocyclic aliphatic heterocyclic group and a polycyclic or condensed ring aliphatic heterocyclic group. As the aliphatic heterocyclic group, illustrative examples thereof include 2-oxo-1-pyrrolidinyl group, piperidino group, piperazinyl group, morpholino group, tetrahydrofuryl group, tetrahydropyranyl group, tetrahydrothienyl group and the like.

These aliphatic heterocyclic groups may have a substituent group, and as the substituent group, the groups described in the description on the substituent group of the alkyl group can be mentioned.

As the acyl group, for example, acetyl group, propanoyl group, butanoyl group, octanoyl group, benzoyl group, toluoyl group, xyloyl group, naphthoyl group, phenanthroyl group, anthroyl group and the like can be mentioned.

These acyl groups may have a substituent group, and as the substituent group, the groups described in the description on the substituent group of the alkyl group can be mentioned.

As the alkoxycarbonyl group, an alkoxycarbonyl group having, for example, from 1 to 30 carbon atoms is desirable, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like.

These alkoxycarbonyl groups may have a substituent group, and as the substituent group, the groups described in the description on the substituent group of the alkyl group can be mentioned.

As the aralkyloxy group, an aralkyloxy group having, for example, from 7 to 12 carbon atoms can be mentioned, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

These aralkyloxy groups may have a substituent group, and as the substituent group, the groups described in the description on the substituent group of the alkyl group can be mentioned.

Regarding the ring formed by $R^3$ and $R^4$, $R^3$ and $R^5$, $R^3$ and $R^6$, $R^4$ and $R^6$ or $R^5$ and $R^6$ in the α,β-unsaturated carbonyl compound represented by the general formula (2) and the optically active carbonyl compound represented by the general formula (3), for example, examples thereof include cyclopentane ring, cyclohexane ring, indane ring, tetralin ring, cyclopentene ring, cyclohexene ring, cycloheptene ring, indene ring, dihydronaphthalene ring, octahydronaphthalene ring, decahydronaphthalene ring and the like. These rings may be substituted with the aforementioned alkyl group or the acyl group described in the following.

As the acyl group as the substituent group of the ring formed by $R^3$ and $R^4$, $R^3$ and $R^5$, $R^3$ and $R^6$, $R^4$ and $R^6$ or $R^5$ and $R^6$, examples thereof include acetyl group, propanoyl group, butanoyl group, octanoyl group, benzoyl group, toluoyl group, xyloyl group, naphthoyl group, phenanthroyl group, anthroyl group and the like.

As illustrative examples of the α,β-unsaturated aldehyde to be used as the substrate in the invention, for example, the following compounds can be mentioned. In this connection, in the case of the presence of Z-configuration and E-configuration regarding the double bond at the α-position and β-position of the α,β-unsaturated aldehyde, all of them are included therein. The wavy line in the following compounds represents Z-configuration, E-configuration or a mixture thereof In the following compounds, Me represents methyl group, and Bn represents benzyl group.

[Chem. 16]

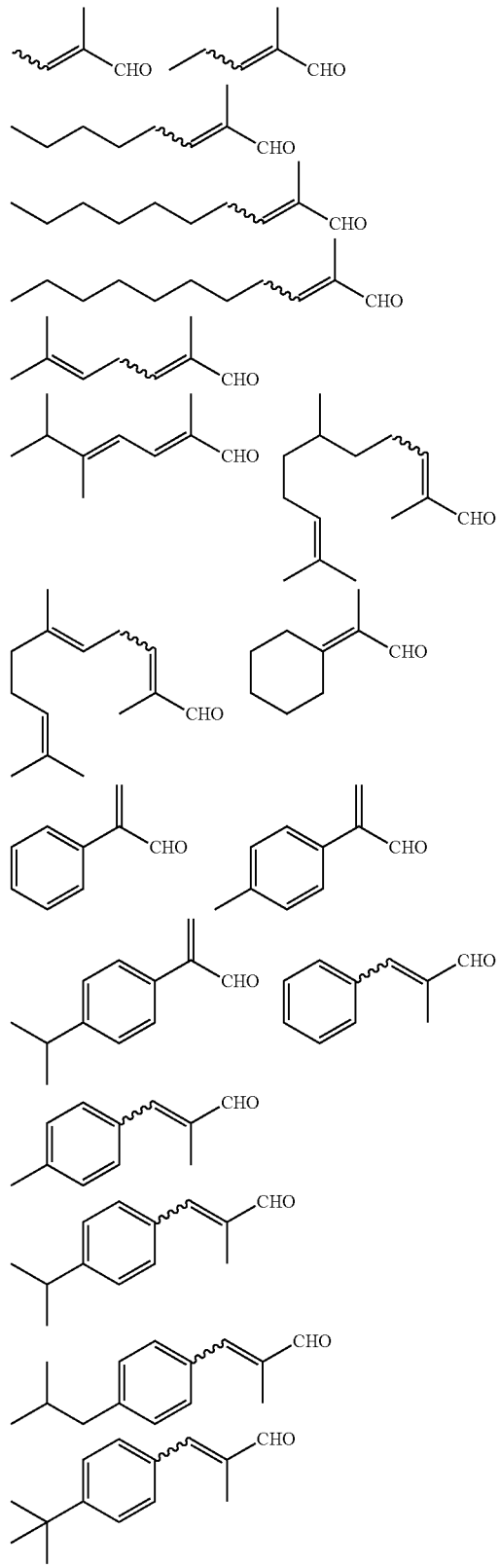

-continued

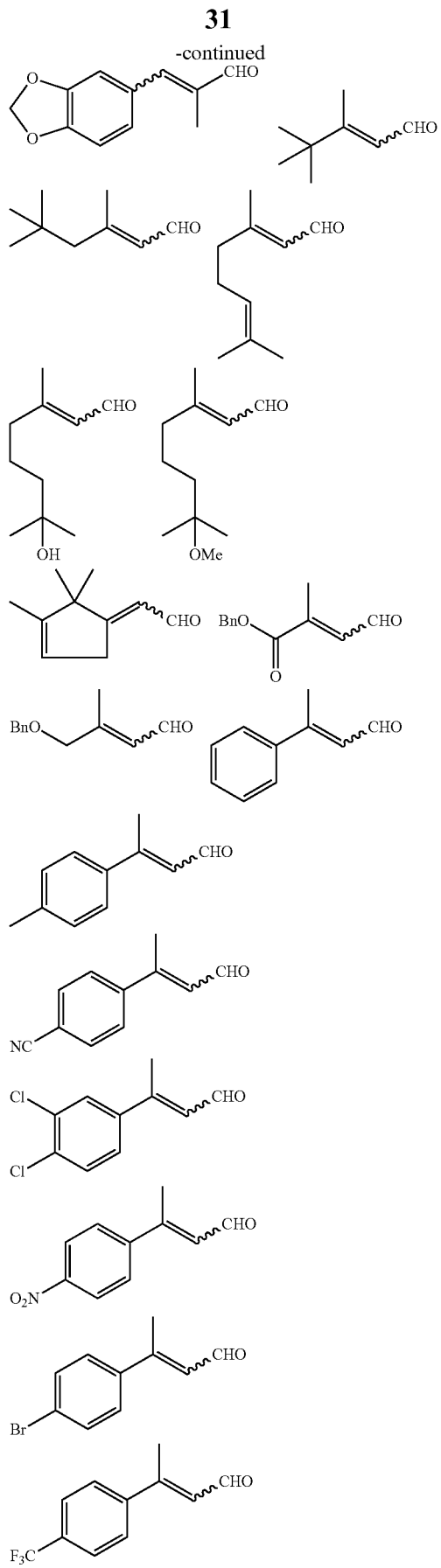

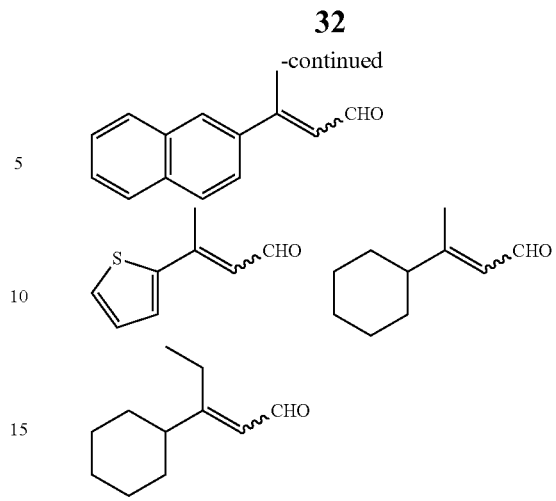

Among the aforementioned α,β-unsaturated aldehydes, geranial (the following A), neral (the following B) and citral can be mentioned as particularly desirable compounds.

[Chem. 17]

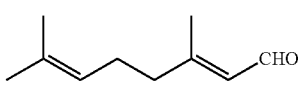

(A)

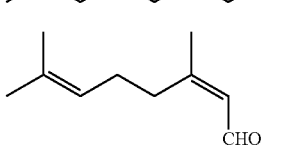

(B)

As the α,β-unsaturated ketone to be used as the substrate in the invention, ketones having 5 to 18 carbon atoms are desirable.

As illustrative examples of the α,β-unsaturated ketone, the following compounds can, for example, be mentioned. In this connection, in the case of the presence of Z-configuration and E-configuration regarding the double bond at the α-position and n-position of the α,β-unsaturated ketone, all of them are included therein. The wavy line in the following compounds represents Z-configuration, E-configuration or a mixture thereof.

In the following compounds, Me represents methyl group, and Ph represents phenyl group, Et represents ethyl group, Bu represents butyl group, Pr represents propyl group and Bn represents benzyl group.

[Chem. 18]

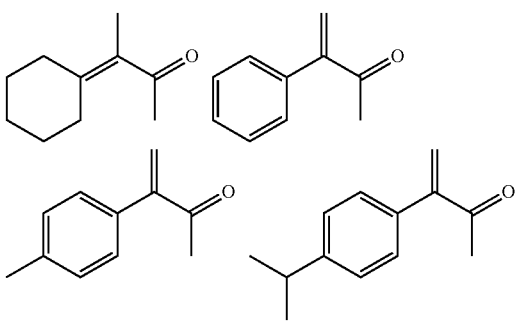

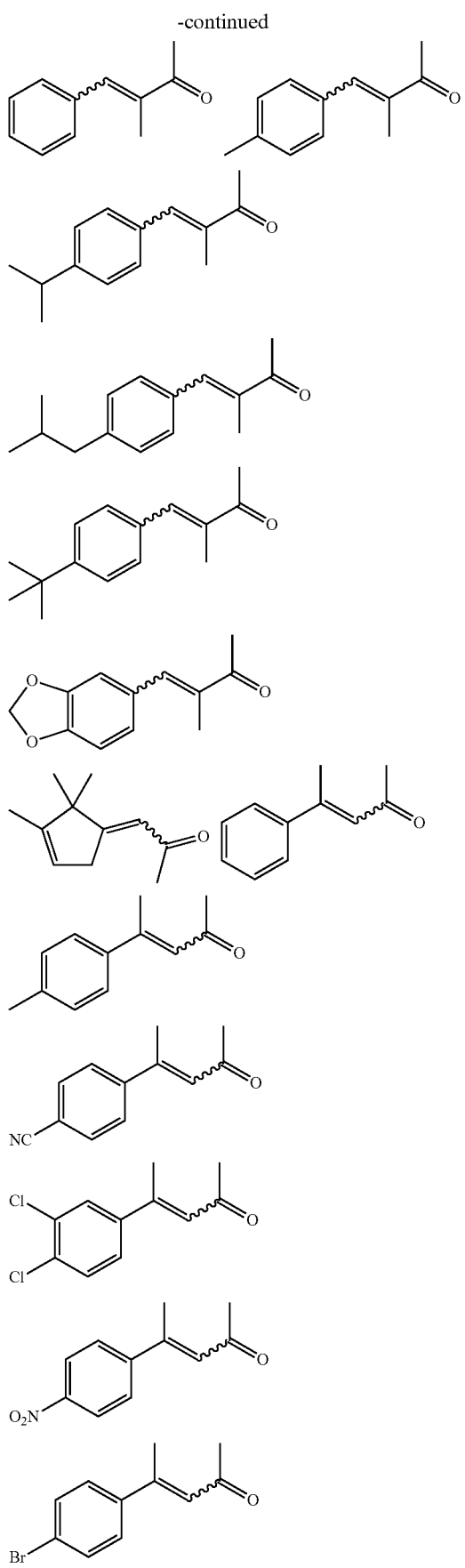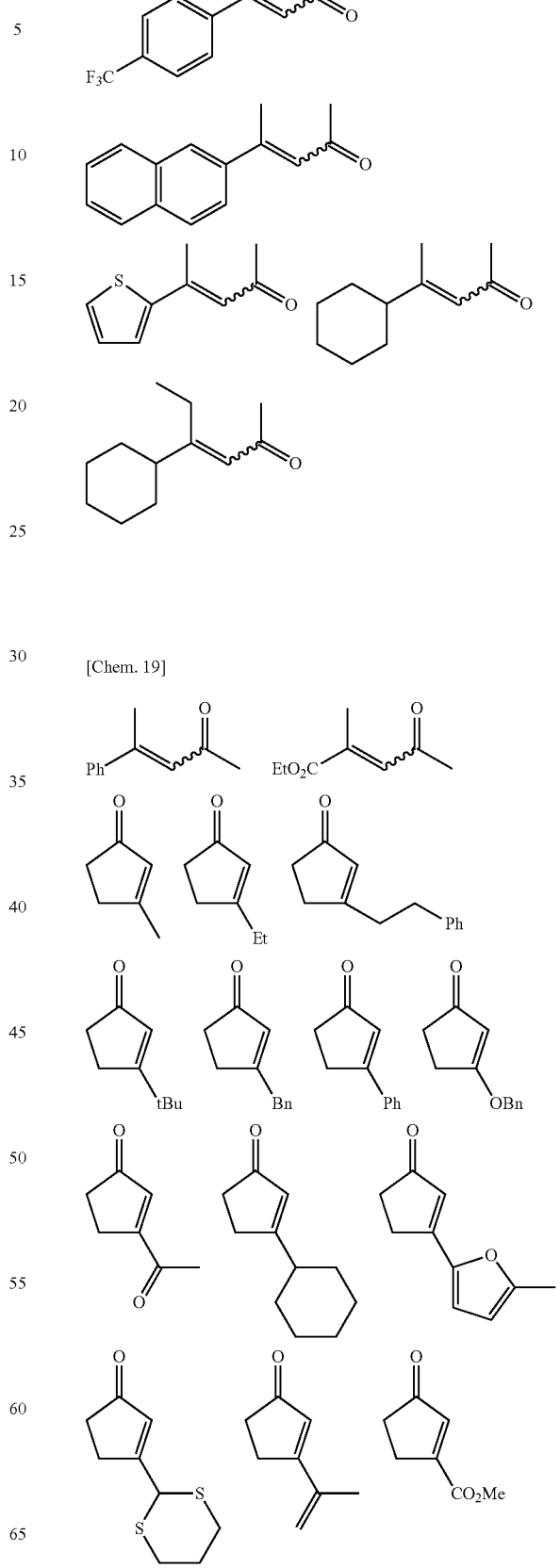

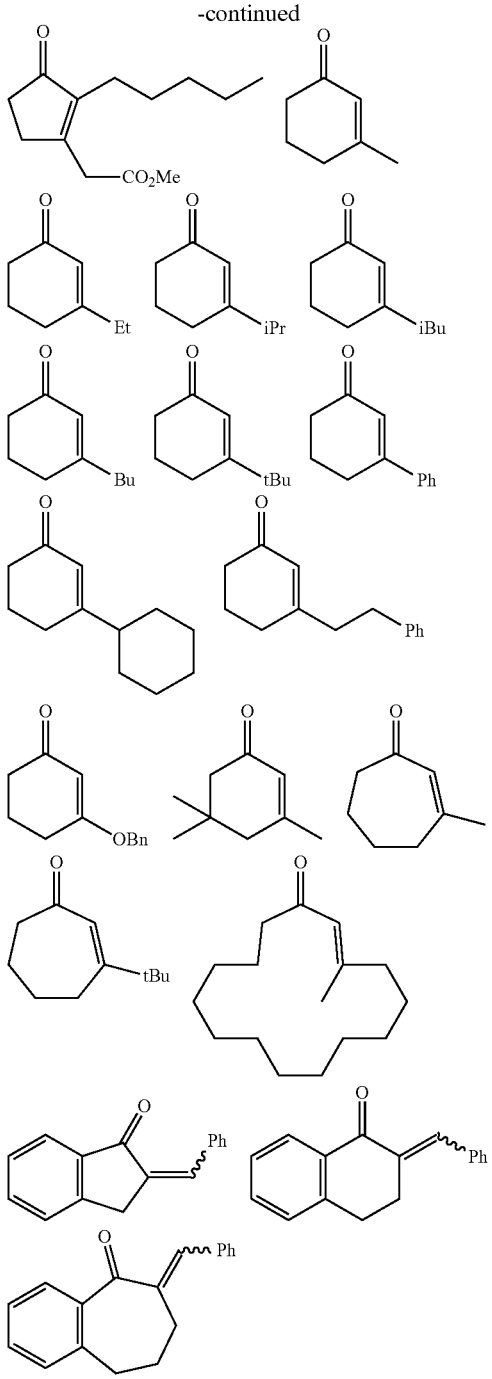

<Production Method of Optically Active Carbonyl Compound>

According to the invention, an optically active carbonyl compound such as an optically active aldehyde or an optically active ketone can be obtained by subjecting an α,β-unsaturated carbonyl compound to asymmetric hydrogenation reaction in the presence of the aforementioned catalyst.

Using amounts of the metal powder and metal-supported substance to be used as catalyst components of the invention vary depending on various reaction conditions, but the total weight of the metal powder or total weight of the metal-supported substance is, for example, from 0.01 to 10% by weight, preferably from 0.02 to 5% by weight, based on the weight of the α,β-unsaturated carbonyl compound as the substrate.

Using amount of the optically active peptide compound to be used as a catalyst component of the invention vary depending on various reaction conditions, but is, for example, from 0.01 to 20% by weight, preferably from 0.04 to 10% by weight, based on the α,β-unsaturated carbonyl compound as the substrate.

Using amount of the acid to be used as catalyst components of the invention vary depending on various reaction conditions, but is, for example, 0.01 to 10 times by mol, preferably 0.2 to 4 times by mol based on the optically active peptide compound.

When an optically active carbonyl compound is produced by carrying out asymmetric hydrogenation of the α,β-unsaturated carbonyl compound using the catalyst of the invention, it can be carried out in the presence or absence of a solvent, but it is desirable to carry it out in the presence of a solvent.

As the illustrative solvent to be used, preferable examples thereof include aliphatic hydrocarbon-based organic solvents such as hexane, heptane and octane; alicyclic hydrocarbon-based organic solvents such as cyclohexane and methylcyclohexane; aromatic hydrocarbon-based organic solvents such as benzene, toluene and xylene; ether-based organic solvents such as diethyl ether, diisopropyl ether, dimethoxyethane, tetrahydrofuran, dioxane and dioxolan; water; alcohol-based organic solvents such as methanol, ethanol, propanol, isopropanol and tertiary butanol; halogenated hydrocarbon-based organic solvents such as dichloromethane, dichloroethane, chlorobenzene and bromotoluene; dimethylformamide, acetonitrile and the like, and a mixed solvent of these solvents can also be used in response to the necessity. Among these solvents, heptane, toluene, tetrahydrofuran, t-butanol and hydrous t-butanol are particularly desirable.

Using amount of the solvent can be optionally selected based on the reaction conditions and the like, but is, for example, from 0 to 20 times volume (mL) [(mL/g)], preferably from 0 to 5 times volume (mL) [(mL/g)], based on the weight (g) of the α,β-unsaturated carbonyl compound as the substrate.

The method of the invention is carried out using hydrogen gas as the hydrogen source, and its hydrogen pressure is from 0.01 MPa to 10 MPa, preferably from 0.1 MPa to 1 MPa. The reaction temperature is from −78 to 100° C., preferably from 10 to 70° C. The reaction time varies depending on the reaction conditions, but is generally from 1 to 30 hours.

The optically active carbonyl compound obtained as described in the above can be isolated and purified by generally used operations such as extraction, recrystallization, various types of chromatography and the like. In addition, regarding configuration of the thus obtained optically active carbonyl compound, its d-form or l-form (R-form or S-form) can be produced by optionally selecting configuration of the optically active peptide compound.

EXAMPLES

The following describes the invention further illustratively based on Synthesis Examples, Examples and Comparative Examples, though the invention is not restricted thereby.

Measurement of the products was carried out by a gas chromatographic method (GLC). The conditions are as described in the following.

The used instrument for analysis: G2010 gas chromatography manufactured by Shimadzu Corp.

Column: DB-WAX (0.25 mm×30 m) manufactured by Agilent for conversion ratio measurement β-DEX-225 (0.25 mm×30 m) manufactured by SUPELCO for optical purity Detector: FID <Synthesis of H-Pro-D-Pro-Aib-Leu-NHPh>

(Synthesis of Optically Active Peptide Compound Used in Examples 1 to 4) (Scheme 1 to 3)

Synthesis Example 1

Segment A: Synthesis of Boc-Pro-D-Pro-OH (Scheme 1)

Synthesis Example 1-1

Synthesis of Boc-Pro-D-Pro-OBn 5.75 g (30.0 mmol) of EDCl was added to 60 ml of tetrahydrofuran (THF) solution of 3.23 g (15.0 mmol) of N-Boc-L-Proline (manufactured by Tokyo Chemical Industry Co., Ltd) and 3.08 g (15.0 mmol) of D-Proline benzylester, followed by stirring for 18 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), it was concentrated under reduced pressure, thereby obtaining crude amide. The obtained amide compound was purified by a silica gel column chromatography (hexane/ethyl acetate=5/1 to 1/1 (volume ratio)), thereby obtaining 4.55 g of the product with a yield of 75.4%.

Synthesis Example 1-2

Synthesis of Boc-Pro-D-Pro-OH 2.05 g of Pd/C (ASCA-2, ca. Pd 5 wt %, 50% wet) was added to 41 ml of methanol solution of 4.10 g (10.2 mmol) of Boc-Pro-D-Pro-OBn obtained in Synthesis Example 1-1, followed by stirring for 20 hours at room temperature under a hydrogen atmosphere. After a reaction mixture was filtrated by celite, the filtrate was concentrated under reduced pressure, thereby obtaining the product with a yield of 100%.

Synthesis Example 2

Synthesis of Segment B: H-Aib-Leu-NHPh (Scheme 2)

Synthesis Example 2-1

Synthesis of Boc-Leu-NHPh 8.43 g (44.0 mmol) of EDCl was added to 100 ml of THF solution of 9.97 g (40.0 mmol) of Boc-Leu-OH (manufactured by Tokyo Chemical Industry Co., Ltd), 3.65 ml (40.0 mmol) of aniline and 4.60 g (40.0 mmol) of HO-Su(hydroxysuccinimide), followed by stirring for 8 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), the organic layer was dried over sodium sulfate. After the drying agent was separated by filtration, the filtrate was concentrated under reduced pressure, thereby obtaining crude amide. The obtained amide compound was purified by a silica gel column chromatography (hexane/ethyl acetate=9/1 to 2/1 (volume ratio)), thereby obtaining 5.43 g of the product with a yield of 44.3%.

Synthesis Example 2-2

Synthesis of H-Leu-NHPh

Under ice-cooling, 3.00 g (9.79 mmol) of Boc-Leu-NHPh obtained in Synthesis Example 2-1 was added to 15.0 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium hydroxide. The water layer was extracted with toluene and an organic layer was washed with brine. After drying over sodium sulfate, a toluene solution was concentrated under reduced pressure, thereby obtaining 2.03 g of the product with a yield of 100%.

Synthesis Example 2-3

Synthesis of Boc-Aib-Leu-NHPh 3.76 g (19.6 mmol) of EDCl was added to 40 ml of THF solution of 1.99 g (9.79 mmol) of Boc-Aib-OH (manufactured by Sigma-Aldrich Corporation), and 2.03 g (9.79 mmol) of H-Leu-NHPh obtained in Synthesis Example 2-2, followed by stirring for 17 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), it was concentrated under reduced pressure, thereby obtaining crude amide. The obtained amide compound was purified by a silica gel column chromatography (hexane/ethyl acetate=5/1 to 1/1 (volume ratio)), thereby obtaining 2.42 g of the product with a yield of 63.1%.

Synthesis Example 2-4

Synthesis of H-Aib-Leu-NHPh

Under ice-cooling, 1.00 g (2.55 mmol) of Boc-Aib-Leu-NHPh obtained in Synthesis Example 2-3 was added to 5 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining 744 mg of the product with a yield of 100%.

Synthesis Example 3

Synthesis of H-Pro-D-Pro-Aib-Leu-NHPh (Segment A+ Segment B) (Scheme 3)

Synthesis Example 3-1

Synthesis of Boc-Pro-D-Pro-Aib-Leu-NHPh 491 mg (2.56 mmol) of EDCl was added to 5 ml of THF solution of 400 mg (1.28 mmol) of Boc-Pro-D-Pro-OH(Segment A) obtained in Synthesis Example 1, 372 mg (1.28 mmol) of H-Aib-Leu-NHPh(Segment B) obtained in Synthesis Example 2, and 196 mg (1.28 mmol) of HO-Bt, followed by stirring for 24 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), the organic layer was dried over sodium sulfate. After the drying agent was separated by filtration, the filtrate was concentrated under reduced pressure, thereby obtaining crude amide. The obtained amide compound was purified by a silica gel column chromatography (hexane/ethyl acetate=3/1 to 0/1 (volume ratio)), thereby obtaining 650 mg of the product with a yield of 86.7%.

Synthesis Example 3-2

Synthesis of H-Pro-D-Pro-Aib-Leu-NHPh

Under ice-cooling, 600 mg (1.02 mmol) of Boc-Pro-D-Pro-Aib-Leu-NHPh obtained in Synthesis Example 3-1 was added to 6 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining crude amine. The obtained amine compound was purified by an alumina column chromatography (ethyl acetate/methanol=10/0 to 10/1 (volume ratio)), thereby obtaining 300 mg of the product with a yield of 60.6%.

<Synthesis of H-Pro-D-Pro-Aib-Trp-NHPh> (Synthesis of the Optically Active Peptide Compound Used in Examples 5 and 6) (Schemes 4 to 5)

Synthesis Example 4

Synthesis of Segment C:H-Aib-Trp-NHPh (Scheme 4)

Synthesis Example 4-1

Synthesis of Boc-Trp-NHPh 4.72 g (24.6 mmol) of EDCl was added to 100 ml of THF solution of 5.00 g (16.4 mmol) of Boc-Trp-OH (manufactured by Tokyo Chemical Industry Co., Ltd), 1.50 ml (16.4 mmol) of aniline and 1.89 g (1.64 mmol) of HO-Su, followed by stirring for 16 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), the organic layer was dried over sodium sulfate. After the drying agent was separated by filtration, the filtrate was concentrated under reduced pressure, thereby obtaining crude amide. The obtained amide compound was purified by a silica gel column chromatography (hexane/ethyl acetate=5/1 to 1/1 (volume ratio)), thereby obtaining 3.10 g of the product with a yield of 49.8%.

Synthesis Example 4-2

Synthesis of H-Trp-NHPh

Under ice-cooling, 2.75 g (7.25 mmol) of Boc-Trp-NHPh obtained in Synthesis Example 4-1 was added to 16.5 ml of a 4N dioxane solution of hydrogen chloride, followed by stirring for 3 hours. After a reaction mixture was concentrated under reduced pressure, dissolution was made by adding water to the concentrate, and a water layer was adjusted to pH=11 an aqueous solution of sodium hydroxide. The water layer was extracted with toluene and an organic layer was washed with brine. After drying over sodium sulfate, a toluene solution was concentrated under reduced pressure, thereby obtaining 2.27 g of the product with a yield of 100%.

Synthesis Example 4-3

Synthesis of Boc-Aib-Trp-NHPh 2.78 g (14.5 mmol) of EDCl was added to 40 ml of THF solution of 1.47 g (7.25 mmol) of Boc-Aib-OH (manufactured by Sigma-Aldrich Corporation), and 2.03 g (7.25 mmol) of H-Trp-NHPh obtained in Synthesis Example 4-2, followed by stirring for 16 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), it was concentrated under reduced pressure, thereby obtaining crude amide. The obtained amide compound was purified by a silica gel column chromatography (hexane/ethyl acetate=3/1 to 0/1 (volume ratio)), thereby obtaining 2.20 g of the product with a yield of 65.3%.

Synthesis Example 4-4

Synthesis of H-Aib-Trp-NHPh

Under ice-cooling, 500 mg (1.08 mmol) of Boc-Aib-Trp-NHPh obtained in Synthesis Example 4-3 was added to 5 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining 337 mg of the product with a yield of 100%.

Synthesis Example 5

Synthesis of H-Pro-D-Pro-Aib-Trp-NHPh (Segment A+ Segment C) (Scheme 5)

Synthesis Example 5-1

Synthesis of Boc-Pro-D-Pro-Aib-Trp-NHPh 414 mg (2.16 mmol) of EDCl was added to 5 ml of THF solution of 337 mg (1.08 mmol) of Boc-Pro-D-Pro-OH(Segment A) obtained in Synthesis Example 1, 420 mg (1.08 mmol) of H-Aib-Trp-NHPh(Segment C) obtained in Synthesis Example 4 and 165 mg (1.08 mmol) of HO-Bt, followed by stirring for 6 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), the organic layer was dried over sodium sulfate. After the drying agent was separated by filtration, the filtrate was concentrated under reduced pressure, thereby obtaining crude amide. The obtained amide compound was purified by a silica gel column chromatography (hexane/ethyl acetate=3/1 to 0/1 (volume ratio)), thereby obtaining 460 mg of the product with a yield of 64.7%.

Synthesis Example 5-2

Synthesis of H-Pro-D-Pro-Aib-Trp-NHPh

Under ice-cooling, 460 mg (0.698 mmol) of Boc-Pro-D-Pro-Aib-Trp-NHPh obtained in Synthesis Example 5-1 was added to 4.6 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining crude amine. The obtained amine compound was purified by an alumina column chromatography (ethyl acetate/methanol=1/0 to 2/1 (volume ratio)), thereby obtaining 340 mg of the product with a yield of 87.2%.

<Synthesis of H-Pro-D-Pro-Aib-Phe-NHPh> (Synthesis of the Optically Active Peptide Compound Used in Example 10) (Schemes 6 to 7)

Synthesis Example 6

Synthesis of Segment D:H-Aib-Phe-NHPh (Scheme 6)

Synthesis Example 6-1

Synthesis of Boc-Phe-NHPh 7.67 g (40.0 mmol) of EDCl was added to 106 ml of THF solution of 5.31 g (20.0 mmol) of Boc-Phe-OH (manufactured by Tokyo Chemical Industry Co., Ltd), 1.82 ml (20.0 mmol) of aniline and 3.06 g (20.0 mmol) of HO-Bt, followed by stirring for 6 hours at room temperature. After a reaction mixture was concentrated under reduced pressure, the concentrate was extracted by adding water and ethyl acetate. After an organic layer was washed sequentially with an aqueous solution of sodium hydrogen carbonate and water (one time for each), the organic layer was dried over sodium sulfate. After the drying agent was separated by filtration, the filtrate was concentrated under reduced pressure, thereby obtaining crude amide. The obtained amide compound was purified by a silica gel column chromatography (toluene/ethyl acetate=9/1 to 7/1 (volume ratio)), thereby obtaining 5.93 g of the product with a yield of 87.1%.

Synthesis Example 6-2

Synthesis of H-Phe-NHPh

Under ice-cooling, 5.00 g (14.7 mmol) of Boc-Phe-NHPh obtained in Synthesis Example 6-1 was added to 25.0 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium hydroxide. The water layer was extracted with toluene and an organic layer was washed with brine. After drying over sodium sulfate, a toluene solution was concentrated under reduced pressure, thereby obtaining 3.53 g of the product with a yield of 100%.

Synthesis Example 6-3

Synthesis of Boc-Aib-Phe-NHPh 4.04 g (22.1 mmol) of EDCl was added to 60 ml of THF solution of 2.99 g (14.7 mmol) of Boc-Aib-OH (manufactured by Sigma-Aldrich Corporation), and 3.53 g (14.7 mmol) of H-Phe-NHPh obtained in Synthesis Example 6-2, followed by stirring for 6 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), it was concentrated under reduced pressure, thereby obtaining crude amide. The obtained amide compound was purified by a silica gel column chromatography (hexane/ethyl acetate=5/1 to 1/1 (volume ratio)), thereby obtaining 5.79 g of the product with a yield of 92.6%.

Synthesis Example 6-4

Synthesis of H-Aib-Phe-NHPh

Under ice-cooling, 1.28 g (3.00 mmol) of Boc-Aib-Phe-NHPh obtained in Synthesis Example 6-3 was added to 6.4 ml of a 4N dioxane solution of hydrogen chloride, followed by stirring for 3 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining 976 mg of the product with a yield of 100%.

Synthesis Example 7

Synthesis of H-Pro-D-Pro-Aib-Phe-NHPh (Segment A+ Segment D) (Scheme 7)

Synthesis Example 7-1

Synthesis of Boc-Pro-D-Pro-Aib-Phe-NHPh 863 mg (4.50 mmol) of EDCl was added to 30 ml of THF solution of 937 mg (3.00 mmol) of Boc-Pro-D-Pro-OH(Segment A) obtained in Synthesis Example 1, 976 mg (3.00 mmol) of H-Aib-Phe-NHPh(Segment D) obtained in Synthesis Example 6 and 459 mg (3.00 mmol) of HO-Bt, followed by stirring for 20 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), the organic layer was dried over sodium sulfate. After the drying agent was separated by filtration, the filtrate was concentrated under reduced pressure, thereby obtaining crude amide. The obtained amide compound was purified by a silica gel column chromatography (hexane/ethyl acetate=5/1 to 0/1 (volume ratio)), thereby obtaining 1.64 g of the product with a yield of 88.2%.

Synthesis Example 7-2

Synthesis of H-Pro-D-Pro-Aib-Phe-NHPh

Under ice-cooling, 1.46 g (2.36 mmol) of Boc-Pro-D-Pro-Aib-Phe-NHPh obtained in Synthesis Example 7-1 was added to 7.3 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining crude amine. The obtained amine compound was purified by an alumina column chromatography (ethyl acetate/methanol=1/0 to 9/1 (volume ratio)), thereby obtaining 800 mg of the product with a yield of 65.2%.
<Synthesis of H-Pro-D-Pro-Aib-Gly-NHPh> (Synthesis of the Optically Active Peptide Compound Used in Example 11) (Schemes 8 to 9)

Synthesis Example 8

Synthesis of Segment E:H-Aib-Gly-NHPh (Scheme8)

Synthesis Example 8-1

Synthesis of Boc-Gly-NHPh 7.67 g (40.0 mmol) of EDCl was added to 50 ml of THF solution of 3.50 g (20.0 mmol) of Boc-Gly-OH (manufactured by Tokyo Chemical Industry Co., Ltd), and 1.82 ml (20.0 mmol) of aniline, followed by stirring for 6 hours at room temperature. After a reaction mixture was concentrated under reduced pressure, the concentrate was extracted by adding water and ethyl acetate. After an organic layer was washed with brine (two times for each), and the organic layer was dried over sodium sulfate. After the drying agent was separated by filtration, the filtrate was concentrated under reduced pressure, thereby obtaining crude amide. The obtained amide compound was purified by a silica gel column chromatography (hexane/ethyl acetate=2/1 to 1/1 (volume ratio)), thereby obtaining 4.85 g of the product with a yield of 96.9%.

Synthesis Example 8-2

Synthesis of H-Gly-NHPh

Under ice-cooling, 4.00 g (16.0 mmol) of Boc-Gly-NHPh obtained in Synthesis Example 8-1 was added to 40.0 ml of a 4N dioxane solution of hydrogen chloride, followed by stirring for 4 hours. After a reaction mixture was concentrated under reduced pressure, dissolution was made by adding water to the concentrate, and a water layer was adjusted to pH=11 by an aqueous solution of sodium hydroxide. The water layer was extracted with ethyl acetate and an organic layer was washed with brine. After drying over sodium sulfate, an ethyl acetate solution was concentrated under reduced pressure, thereby obtaining 2.10 g of the product with a yield of 87.4%.

Synthesis Example 8-3

Synthesis of Boc-Aib-Gly-NHPh 2.14 g (21.0 mmol) of EDCl was added to 210 ml of THF solution of 2.85 g (14.0 mmol) of Boc-Aib-OH (manufactured by Sigma-Aldrich Corporation), and 2.10 g (14.0 mmol) of H-Gly-NHPh obtained in Synthesis Example 8-2, followed by stirring for 8 hours at room temperature. After a reaction mixture was concentrated under reduced pressure, the concentrate was extracted by adding water and ethyl acetate. After an organic layer was washed sequentially with water, an aqueous solution of sodium hydrogen carbonate and water (two times for each), it was concentrated under reduced pressure, thereby obtaining 4.38 g of amide of the product with a yield of 93.2%.

Synthesis Example 8-4

Synthesis of H-Aib-Gly-NHPh

Under ice-cooling, 1.01 g (3.00 mmol) of Boc-Aib-Gly-NHPh obtained in Synthesis Example 8-3 was added to 10.0 ml of a 4N dioxane solution of hydrogen chloride, followed by stirring for 3 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining 706 mg of the product with a yield of 100%.

Synthesis Example 9

Synthesis of H-Pro-D-Pro-Aib-Gly-NHPh (Segment A+ Segment E) (Scheme9)

Synthesis Example 9-1

Synthesis of Boc-Pro-D-Pro-Aib-Gly-NHPh 863 mg (4.50 mmol) of EDCl was added to 30 ml of THF solution of 937 mg (3.00 mmol) of Boc-Pro-D-Pro-OH(Segment A) obtained in Synthesis Example 1, 706 mg (3.00 mmol) of H-Aib-Gly-NHPh(Segment E) obtained in Synthesis Example 8, and 459 mg (3.00 mmol) of HO-Bt, followed by stirring for 20 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), and the organic layer was dried over sodium sulfate. After the drying agent was separated by filtration, the filtrate was concentrated under reduced pressure, thereby obtaining crude amide. The obtained amide compound was purified by a silica gel column chromatography (ethyl acetate/methanol=1/0 to 19/1 (volume ratio)), thereby obtaining 1.06 g of the product with a yield of 66.7%.

Synthesis Example 9-2

Synthesis of H-Pro-D-Pro-Aib-Gly-NHPh

Under ice-cooling, 960 mg (1.81 mmol) of Boc-Pro-D-Pro-Aib-Gly-NHPh obtained in Synthesis Example 9-1 was added to 6.7 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining crude amine. The obtained amine compound was purified by an alumina column chromatography (ethyl acetate/methanol=1/0 to 9/1 (volume ratio)), thereby obtaining 480 mg of the product with a yield of 61.7%.

Synthesis Example 10

Synthesis of H-Pro-Pro-NHPh (Synthesis of the Optically Active Peptide Compound Used in Example 7) (Scheme 10)

Synthesis Example 10-1

Synthesis of Boc-Pro-Pro-NHPh 201 mg (1.05 mmol) of EDCl was added to 5 ml of THF solution of 100 mg (0.526 mmol) of Boc-Pro-OH (manufactured by Tokyo Chemical Industry Co., Ltd), and 113 mg (0.526 mmol) of H-Pro-NHPh (manufactured by Tokyo Chemical Industry Co., Ltd), followed by stirring for 6 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), it was concentrated under reduced pressure, thereby obtaining crude amide. The obtained amide compound was purified by a silica gel column chromatography (hexane/ethyl acetate=5/1 to 1/1 (volume ratio)), thereby obtaining 150 mg of the product with a yield of 73.6%.

Synthesis Example 10-2

Synthesis of H-Pro-Pro-NHPh

Under ice-cooling, 150 mg (0.387 mmol) of Boc-Pro-Pro-NHPh obtained in Synthesis Example 10-1 was added to 1.5 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining 27 mg of the product with a yield of 24.3%.

Synthesis Example 11

Synthesis of H-Pro-D-Pro-NHPh (Synthesis of the Optically Active Peptide Compound Used Examples 8 and 9) (Scheme 11)

Synthesis Example 11-1

Synthesis of Boc-Pro-D-Pro-NHPh 201 mg (1.05 mmol) of EDCl was added to 5 ml of THF solution of 100 mg (0.526 mmol) of Boc-Pro-OH (manufactured by Tokyo Chemical Industry Co., Ltd), and 113 mg (0.526 mmol) of H-D-Pro-NHPh (manufactured by Tokyo Chemical Industry Co., Ltd), followed by stirring for 6 hours at room temperature. After a reaction mixture was concentrated under reduced pressure, the concentrate was extracted by adding water and ethyl acetate. After an organic layer was washed sequentially with a diluted hydrochloric acid, an aqueous solution of sodium hydrogen carbonate and water (one time for each), it was concentrated under reduced pressure, thereby obtaining crude amide. The obtained amide compound was purified by a silica gel column chromatography (hexane/ethyl acetate=5/1 to 1/1 (volume ratio)), thereby obtaining 160 mg of the product with a yield of 73.6%.

Synthesis Example 11-2

Synthesis of H-Pro-D-Pro-NHPh

Under ice-cooling, 160 mg (0.413 mmol) of Boc-Pro-D-Pro-NHPh obtained in Synthesis Example 11-1 was added to 1.6 ml of a 4N dioxane solution of hydrogen chloride, followed by stirring for 2 hours. After a reaction mixture was concentrated under reduced pressure, dissolution was made by adding water to the concentrate, and a water layer was adjusted to pH=11 by an aqueous solution of sodium carbonate. The water layer was extracted with ethyl acetate and an organic layer was washed with brine. After drying over sodium sulfate, an ethyl acetate solution was concentrated under reduced pressure, thereby obtaining 60 mg of the product with a yield of 50.5%.

Example 1

2 g (13.14 mmol) of citral (geranial:neral=50:50), 25 mg of 5% by weight Pd/barium sulfate (1.25% by weight based on citral), 100 mg of H-Pro-D-Pro-Aib-Leu-NHPh (0.21 mmol, 5.0% by weight based on citral), 23.5 mg (0.21 mmol) of trifluoroacetic acid, and 4 ml of 10% by weight hydrous t-butanol were put into a 50 ml reaction flask, followed by stirring under an atmosphere of hydrogen. After stirring at 40° C. for 21 hours and subsequent removal of the catalyst by filtration, the resulting filtrate was analyzed by a gas chromatography to find that conversion ratio of citral into citronellal was 25.6%, the thus obtained citronellal was l-form and its optical purity was 61.6% e.e.

Example 2

2 g (13.14 mmol) of citral (geranial:neral=50:50), 25 mg of 5% by weight Pd/barium sulfate (1.25% by weight based on citral), 100 mg of H-Pro-D-Pro-Aib-Leu-NHPh (0.21 mmol, 5.0% by weight based on citral), 23.5 mg (0.21 mmol) of trifluoroacetic acid, and 4 ml of 10% by weight hydrous t-butanol were put into a 50 ml reaction flask, followed by stirring under an atmosphere of hydrogen. After stirring at 50°

C. for 21 hours and subsequent removal of the catalyst by filtration, the resulting filtrate was analyzed by a gas chromatography to find that conversion ratio of citral into citronellal was 64.1%, the thus obtained citronellal was l-form and its optical purity was 61.4% e.e.

Example 3

2 g (13.14 mmol) of geranial, 25 mg of 5% by weight Pd/silica-alumina (1.25% by weight based on geranial), 100 mg of H-Pro-D-Pro-Aib-Leu-NHPh (0.21 mmol, 5.0% by weight based on geranial), 23.5 mg (0.21 mmol) of trifluoroacetic acid, and 4 ml of toluene were put into a 50 ml reaction flask, followed by stirring under an atmosphere of hydrogen. After stirring at 25° C. for 21 hours and subsequent removal of the catalyst by filtration, the resulting filtrate was analyzed by a gas chromatography to find that conversion ratio of geranial into citronellal was 3.9%, the thus obtained citronellal was l-form and its optical purity was 30.4% e.e.

Example 4

2 g (13.14 mmol) of geranial, 25 mg of 5% by weight Pd/zeolite (1.25% by weight based on geranial), 100 mg of H-Pro-D-Pro-Aib-Leu-NHPh (0.21 mmol, 5.0% by weight based on geranial), 23.5 mg (0.21 mmol) of trifluoroacetic acid, and 4 ml of toluene were put into a 50 ml reaction flask, followed by stirring under an atmosphere of hydrogen. After stirring at 25° C. for 21 hours and subsequent removal of the catalyst by filtration, the resulting filtrate was analyzed by a gas chromatography to find that conversion ratio of geranial into citronellal was 41.0%, the thus obtained citronellal was l-form and its optical purity was 14.7% e.e.

Example 5

2 g (13.14 mmol) of citral (geranial:neral=50:50), 25 mg of 5% by weight Pd/barium sulfate (1.25% by weight based on citral), 120 mg of H-Pro-D-Pro-Aib-Trp-NHPh (0.22 mmol, 6.0% by weight based on citral), 24.5 mg (0.22 mmol) of trifluoroacetic acid, and 4 ml of 10% by weight hydrous t-butanol were put into a 50 ml reaction flask, followed by stirring under an atmosphere of hydrogen. After stirring at 40° C. for 21 hours and subsequent removal of the catalyst by filtration, the resulting filtrate was analyzed by a gas chromatography to find that conversion ratio of citral into citronellal was 20.0%, the thus obtained citronellal was l-form and its optical purity was 44.0% e.e.

Example 6

2 g (13.14 mmol) of citral (geranial:neral=50:50), 25 mg of 5% by weight Pd/barium sulfate (1.25% by weight based on citral), 120 mg of H-Pro-D-Pro-Aib-Trp-NHPh (0.22 mmol, 6.0% by weight based on citral), 24.5 mg (0.22 mmol) of trifluoroacetic acid, and 4 ml of 10% by weight hydrous t-butanol were put into a 50 ml reaction flask, followed by stirring under an atmosphere of hydrogen. After stirring at 50° C. for 21 hours and subsequent removal of the catalyst by filtration, the resulting filtrate was analyzed by a gas chromatography to find that conversion ratio of citral into citronellal was 28.3%, the thus obtained citronellal was l-form and its optical purity was 46.5% e.e.

Example 7

2 g (13.14 mmol) of geranial, 25 mg of 5% by weight Pd/barium sulfate (1.25% by weight based on geranial), 70 mg of H-Pro-Pro-NHPh (0.24 mmol, 3.5% by weight based on geranial), 27.8 mg (0.24 mmol) of trifluoroacetic acid, and 4 ml of toluene were put into a 50 ml reaction flask, followed by stirring under an atmosphere of hydrogen. After stirring at 25° C. for 21 hours and subsequent removal of the catalyst by filtration, the resulting filtrate was analyzed by a gas chromatography to find that conversion ratio of geranial into citronellal was 6.9%, the thus obtained citronellal was l-form and its optical purity was 10.9% e.e.

Example 8

2 g (13.14 mmol) of geranial, 25 mg of 5% by weight Pd/silica-alumina (1.25% by weight based on geranial), 70 mg of H-Pro-D-Pro-NHPh (0.24 mmol, 3.5% by weight based on geranial), 27.8 mg (0.24 mmol) of trifluoroacetic acid, and 4 ml of toluene were put into a 50 ml reaction flask, followed by stirring under an atmosphere of hydrogen. After stirring at 25° C. for 21 hours and subsequent removal of the catalyst by filtration, the resulting filtrate was analyzed by a gas chromatography to find that conversion ratio of geranial into citronellal was 4.9%, the thus obtained citronellal was l-form and its optical purity was 15.0% e.e.

Example 9

2 g (13.14 mmol) of geranial, 25 mg of 5% by weight Pd/zeolite (1.25% by weight based on geranial), 70 mg of H-Pro-D-Pro-NHPh (0.24 mmol, 3.5% by weight based on geranial), 27.8 mg (0.24 mmol) of trifluoroacetic acid, and 4 ml of toluene were put into a 50 ml reaction flask, followed by stirring under an atmosphere of hydrogen. After stirring at 25° C. for 21 hours and subsequent removal of the catalyst by filtration, the resulting filtrate was analyzed by a gas chromatography to find that conversion ratio of geranial into citronellal was 5.7%, the thus obtained citronellal was l-foam and its optical purity was 7.3% e.e.

Example 10

2 g (13.14 mmol) of citral (geranial:neral=50:50), 25 mg of 5% by weight Pd/barium sulfate (1.25% by weight based on citral), 120 mg of H-Pro-D-Pro-Aib-Phe-NHPh (0.23 mmol, 6.0% by weight based on citral), 26.3 mg (0.23 mmol) of trifluoroacetic acid, and 4 ml of 10% by weight hydrous t-butanol were put into a 50 ml reaction flask, followed by stirring under an atmosphere of hydrogen. After stirring at 50° C. for 21 hours and subsequent removal of the catalyst by filtration, the resulting filtrate was analyzed by a gas chromatography to find that conversion ratio of citral into citronellal was 38.0%, the thus obtained citronellal was l-form and its optical purity was 54.1% e.e.

Example 11

2 g (13.14 mmol) of citral (geranial:neral=50:50), 25 mg of 5% by weight Pd/barium sulfate (1.25% by weight based on citral), 100 mg of H-Pro-D-Pro-Aib-Gly-NHPh (0.23 mmol, 5.0% by weight based on citral), 26.5 mg (0.23 mmol) of trifluoroacetic acid, and 4 ml of 10% by weight hydrous t-butanol were put into a 50 ml reaction flask, followed by stirring under an atmosphere of hydrogen. After stirring at 50° C. for 21 hours and subsequent removal of the catalyst by filtration, the resulting filtrate was analyzed by a gas chromatography to find that conversion ratio of citral into citronellal was 48.2%, the thus obtained citronellal was l-form and its optical purity was 38.5% e.e.

TABLE 1
| Ex. | Optically active peptide compound | Catalyst; Temp.; Solvent | Conversion ratio (%) | Configuration of citronellal | Optical purity (% e.e.) |
|---|---|---|---|---|---|
| 1 | 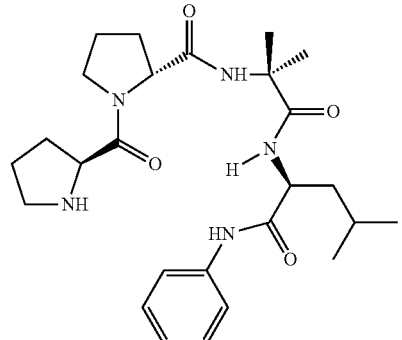<br>H-Pro-D-Pro-Aib-Leu-NHPh | 5 wt % Pd/BaSO₄; 40° C.; 10 wt % hydrous t-butanol | 25.6 | l | 61.6 |
| 2 | 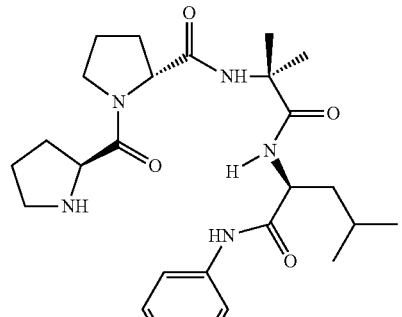<br>H-Pro-D-Pro-Aib-Leu-NHPh | 5 wt % Pd/BaSO₄; 50° C.; 10 wt % hydrous t-butanol | 64.1 | l | 61.4 |
| 3 | 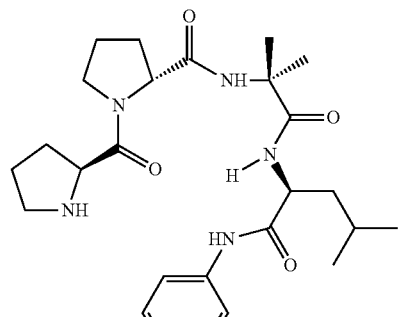<br>H-Pro-D-Pro-Aib-Leu-NHPh | 5 wt % Pd/silica-alumina; 25° C.; toluene | 3.9 | l | 30.4 |

TABLE 2

| Ex. | Optically active peptide compound | Catalyst; Temp.; Solvent | Conversion ratio (%) | Configuration of citronellal | Optical purity (% e.e.) |
|---|---|---|---|---|---|
| 4 | 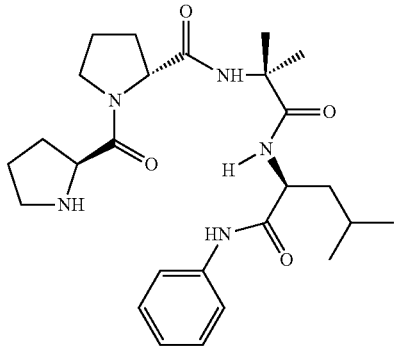<br>H-Pro-D-Pro-Aib-Leu-NHPh | 5 wt % Pd/zeolite; 25° C.; toluene | 41.0 | l | 14.7 |
| 5 | 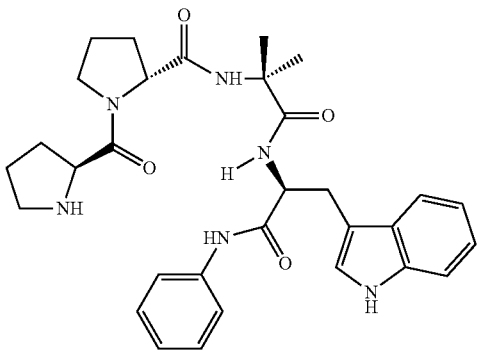<br>H-Pro-D-Pro-Aib-Trp-NHPh | 5 wt % Pd/BaSO$_4$; 40° C.; 10 wt % hydrous t-butanol | 20.0 | l | 44.0 |

TABLE 3

| Ex. | Optically active peptide compound | Catalyst; Tempe.; Solvent | Conversion ratio (%) | Configuration of citronellal | Optical purity (% e.e.) |
|---|---|---|---|---|---|
| 6 | 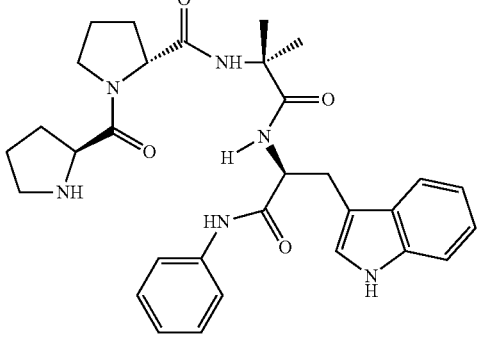<br>H-Pro-D-Pro-Aib-Trp-NHPh | 5 wt % Pd/BaSO$_4$; 50° C.; 10 wt % hydrous t-butanol | 28.3 | l | 46.5 |

TABLE 3-continued

| Ex. | Optically active peptide compound | Catalyst; Tempe.; Solvent | Conversion ratio (%) | Configuration of citronellal | Optical purity (% e.e.) |
|---|---|---|---|---|---|
| 7 | 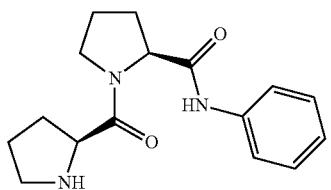 H-Pro-Pro-NHPh | 5 wt % Pd/BaSO₄; 25° C.; toluene | 6.9 | l | 10.9 |
| 8 | 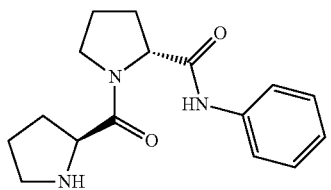 H-Pro-D-Pro-NHPh | 5 wt % Pd/silica-alumina; 25° C.; toluene | 4.9 | l | 15.0 |

TABLE 4

| Ex. | Optically active peptide compound | Catalyst; Temp.; Solvent | Conversion ratio (%) | Configuration of citronellal | Optical purity (% e.e.) |
|---|---|---|---|---|---|
| 9 | 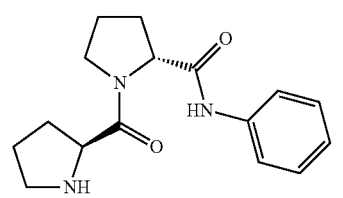 H-Pro-D-Pro-NHPh | 5 wt % Pd/zeolite; 25° C.; toluene | 5.7 | l | 7.3 |
| 10 | 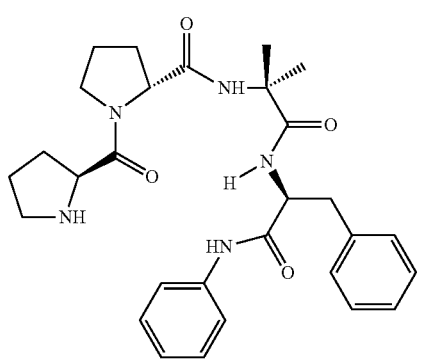 H-Pro-D-Pro-Aib-Phe-NHPh | 5 wt % Pd/BaSO₄; 50° C.; 10 wt % hydrous t-butanol | 38.0 | l | 54.1 |

TABLE 4-continued

| Ex. | Optically active peptide compound | Catalyst; Temp.; Solvent | Conversion ratio (%) | Configuration of citronellal | Optical purity (% e.e.) |
|---|---|---|---|---|---|
| 11 | 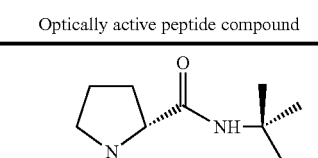<br>H-Pro-D-Pro-Aib-Gly-NHPh | 5 wt % Pd/BaSO$_4$; 50° C.; 10 wt % hydrous t-butanol | 48.2 | 1 | 38.5 |

The catalyst for asymmetric hydrogenation to be used in the invention, which is prepared by simply mixing a metal powder or metal-supported substance, an optically active peptide compound and an acid, can produce an optically active α,β-carbonyl compound by conveniently carrying out asymmetric hydrogenation of its substrate, an α,β-unsaturated carbonyl compound.

That is, optically active citronellal can be obtained by conducting selective asymmetric hydrogenation of α,β-carbon-carbon double bond of citral (a mixture of geranial and neral), geranial or neral. The optically active citronellal is not only useful by itself as a flavor or fragrance but is also an important raw material of optically active citronellol, optically active isopulegol and optically active menthol.

According to the invention, even when a mixture (so-called citral) of the Z-configuration compound and E-configuration compound is used as the substrate, there is no need to carry out the asymmetric hydrogenation after the citral is distilled to obtain neral or geranial with high purity. Accordingly, an optically active carbonyl compound having the same configuration can be produced.

In addition, since the catalyst of the invention is not soluble in the reaction mixture, the metal or metal-supported substance and optically active peptide compound can be easily recovered from the reaction system and recycled, which is industrially advantageous.

What is claimed is:

1. A method for manufacturing an optically active carbonyl compound represented by the following general formula (3):

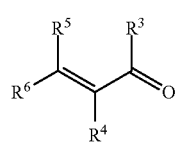

(3)

wherein $R^3$, $R^4$, $R^5$ and $R^6$ are the same as defined in the following formula (2), and two * mean that at least one * represents an asymmetric carbon atom, wherein the method comprises conducting asymmetric hydrogenation of an α,β-unsaturated carbonyl compound represented by the following general formula (2) by using a catalyst for asymmetric hydrogenation:

(2)

wherein $R^3$, $R^4$, $R^5$ and $R^6$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, an alkoxycarbonyl group which may have a substituent group or an aralkyloxy group which may have a substituent group; $R^3$ and $R^4$, $R^3$ and $R^5$, $R^3$ and $R^6$, $R^4$ and $R^6$ or $R^5$ and $R^6$ may form a ring; and when a ring is not formed by $R^3$ and $R^4$ or $R^3$ and $R^5$, and $R^4$ does not represent a hydrogen atom, $R^5$ and $R^6$ may be the same or different from each other; and when a ring is not formed by $R^3$ and $R^4$ or $R^3$ and $R^5$, and $R^4$ represents a hydrogen atom, $R^5$ and $R^6$ do not represent a hydrogen atom and are different from each other, wherein said catalyst for asymmetric hydrogenation comprises:
a powder of at least one metal selected from metals belonging to Group 8 to Group 10 of the Periodic Table, or a metal-supported substance in which at least one metal selected from metals belonging to Group 8 to Group 10 of the Periodic Table is supported on a support;
an optically active peptide compound represented by the following general formula (1):

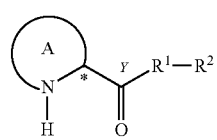

(1)

wherein ring A is a 3- to 7-membered ring which may have a substituent group, contains at least one atom selected from the group consisting of a carbon atom, a nitrogen atom, a sulfur atom, an oxygen atom and a phosphorus atom, and may be a fused ring structure; $R^1$ represents an amino acid residue which is bonded to a carbonyl group at Y-position by a peptide bond or a peptide residue which is constituted from 2 to 30 amino acids and is bonded to a carbonyl group at Y-position by a peptide bond; $R^2$ represents an amino group which is bonded to a carbonyl group at C-terminus of $R^1$, an alkoxy group which is bonded to a carbonyl group at C-terminus of $R^1$, a hydroxy group which is bonded to a carbonyl group at C-terminus of $R^1$ or a polymer chain which is bonded to a carbonyl group at C-terminus of $R^1$, and * represents an asymmetric carbon atom; and an acid.

2. The method according to claim 1, wherein the α,β-unsaturated carbonyl compound is geranial, neral or citral.

3. The method according to claim 1, wherein the α,β-unsaturated carbonyl compound is an α,β-unsaturated ketones having from 5 to 18 carbon atoms.

4. The method according to claim 1, wherein the metal is selected from the group consisting of nickel, ruthenium, rhodium, iridium, palladium and platinum.

* * * * *